(12) United States Patent
Wagner et al.

(10) Patent No.: US 8,287,881 B2
(45) Date of Patent: Oct. 16, 2012

(54) SYNTHETIC GAGPOL GENES AND THEIR USES

(75) Inventors: Ralf Wagner, Regensburg (DE); Markus Graf, Friedberg (DE); Ludwig Deml, Regentauf (DE); Kurt Bieler, Regensburg (DE)

(73) Assignee: GENEART AG, Regensburg (DE)

( * ) Notice: Subject to any disclaimer, the term of this patent is extended or adjusted under 35 U.S.C. 154(b) by 1168 days.

(21) Appl. No.: 11/754,755

(22) Filed: May 29, 2007

(65) Prior Publication Data

US 2007/0293448 A1 Dec. 20, 2007

Related U.S. Application Data

(63) Continuation of application No. 10/276,482, filed as application No. PCT/EP01/05744 on May 18, 2001, now Pat. No. 7,378,515.

(30) Foreign Application Priority Data

May 18, 2000 (EP) .................................... 00110623

(51) Int. Cl.
*A61K 39/21* (2006.01)
*C12N 15/00* (2006.01)
*C07H 21/04* (2006.01)

(52) U.S. Cl. ................ 424/207.1; 435/320.1; 536/23.72

(58) Field of Classification Search ........................ None
See application file for complete search history.

(56) References Cited

FOREIGN PATENT DOCUMENTS

| WO | WO 98/34640 | 8/1998 |
|----|-------------|--------|
| WO | WO 00/15819 | 3/2000 |
| WO | WO 00/39304 | 7/2000 |

OTHER PUBLICATIONS

Kotsopoulou, E., et al., A Rev-independent human immunodeficiency virus type 1 (HIV-1)-based vector that exploits a codon-optimized HIV-1 gag-pol gene, J. Virol. 74(10):4839-4852.*

Mitrophanous, K. A., et al., 1999, Stable gene transfer to the nervous system using a non-primate lentiviral vector, Gene Therapy 6:1808-1818.*
Gallo, R. C., 2005, The end or the beginning of the drive to an HIV-preventive vaccine: a view from over 20 years, The Lancet 366(9500):1894-1898.*
Walker, B. D., and D. R. Burton, 2008, Toward an AIDS vaccine, Science 320:760-764.*
2006 Instructions to Authors, *J. Virol.*, 80:1-17, 2006.
Ellington and Cherry, "Characteristics of Amino Acids," *Curr. Prot. Molec. Biol.*, A.1C.1-A.1C.12, 1997.
Graf et al., "Concerted action of multiple cis-acting sequences is required for rev dependence of late human immunodeficiency type 1 gene expression," *J. Virol.*, 74:10822-10826, 2000.
Haas et al., "Codon usage limitation in the expression of HIV-1 envelope glycoprotein," *Curr. Biol.*, 6:315-324, 1996.
Kotsopoulou et al., "A rev-independent human immunodeficiency virus type 1 (HIV-1)-based vector that exploits a codon-optimized HIV-1 gag-pol gene," *J. Virol.*, 74:4839-4852, 2000.
Luban and Goff, "Mutational analysis of cis-acting packaging signals in human immunodeficiency virus type I RNA," *J. Virol.*, 68:3784-3793, 1994.
Murphy, "Virus Taxonomy," In: Fields Virology, Third Edition (Fields et al., eds.) Lippincott-Raven Publishers, Philadelphia, pp. 40-41, 1996.
Qiu et al., "Evaluation of novel human immunodeficiency virus type 1 gag DNA vaccines for protein expression in mammalian cells and induction of immune responses," *J. Virol.*, 73:9145-9152, 1999.
Schneider et al., "Inactivation of the human immunodeficiency virus type inhibitory elements allows rev-independent expression of gag and gag/protease and particle formation," *J. Virol.*, 71:4892-4903, 1997.
Schwartz et al., "Mutational inactivation of an inhibitory sequence in human immunodeficiency virus type 1 results in rev-independent gag expression," *J. Virol.*, 66:7176-7182, 1992.
Xiang et al., "Translational recoding signals between gag and pol in diverse LTR retrotransposons," RNA, 9:1422-1430, 2003.

* cited by examiner

*Primary Examiner* — Jeffrey S. Parkin

(57) ABSTRACT

The present invention relates to synthetic gag and gagpol genes optimized for high level expression via codon optimization and the uses thereof for the efficient generation of vector particles. The invention further relates to the generation of packaging cells and vaccines based on the synthetic gag and gagpol genes.

18 Claims, 14 Drawing Sheets

Fig. 2A

Figure 1:
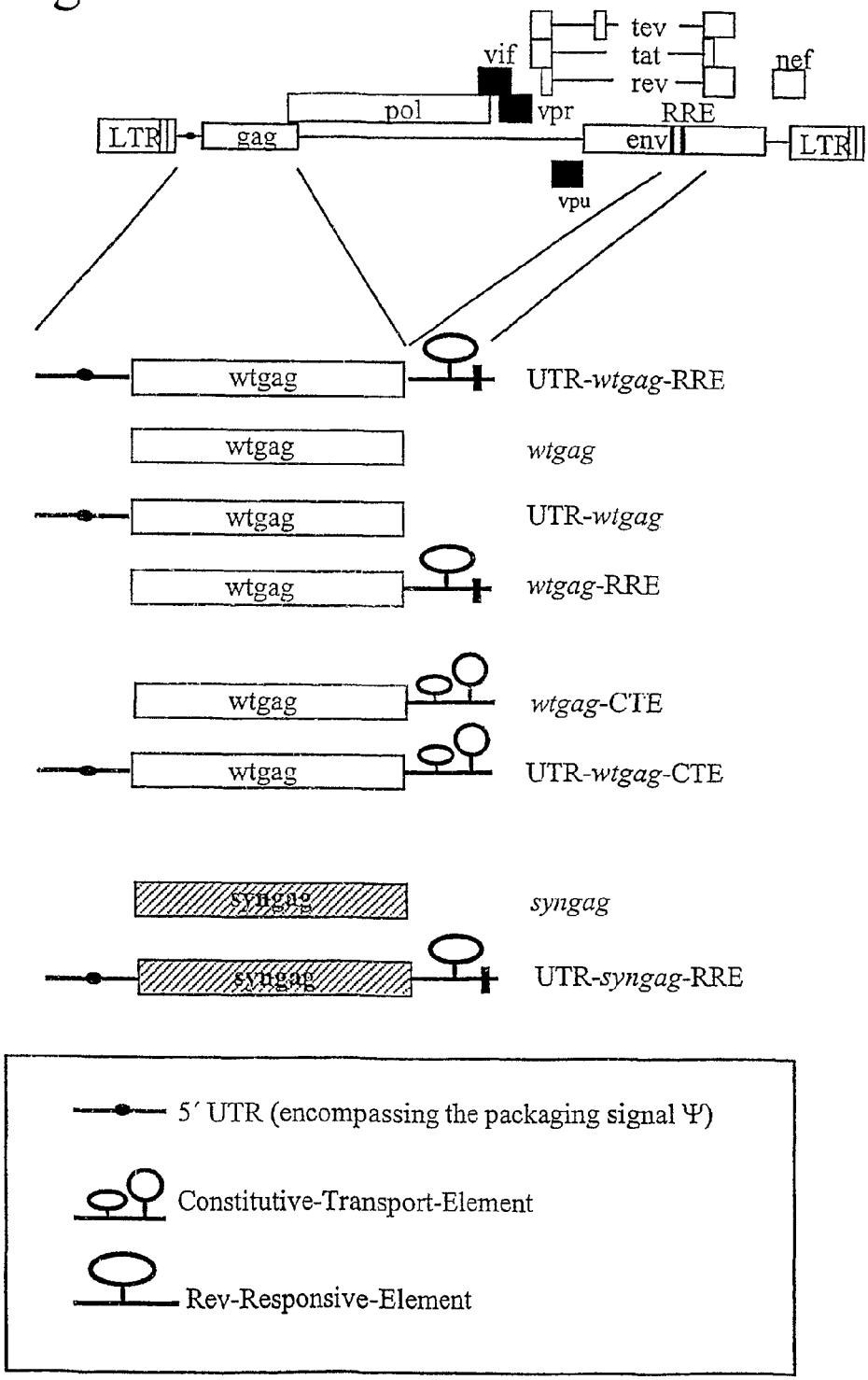

```
  1 ATGGGTGCGAGAGCGTCAGTATTAAGCGGGGGAGAATTAGATCGATGGGA 50
    |||||  ||  || ||      ||  |  |||||  ||  ||   |  ||   | |||||
    ATGGGCGCCAGGGCCAGCGTGCTGAGCGGCGGCGAGCTGGACAGGTGGGA

51 AAAAATTCGGTTAAGGCCAGGGGGAAAGAAAAAATATAAATTAAAACATA 100
    ||  ||   ||  |  |||||  ||  ||  |||||| ||  |||||   |  || ||  |
    GAAGATCAGGCTGAGGCCCGGCGGCAAGAAGAAGTATAAGCTGAAGCACA

101 TAGTATGGGCAAGCAGGGAGCTAGAACGATTCGCAGTTAATCCTGGCCTG 150
    |  ||   ||||||   ||||||||||| ||   |  ||||| ||  || ||  ||||||
    TCGTGTGGGCCAGCAGGGAGCTGGAGAGGTTCGCCGTGAACCCCGGCCTG

151 TTAGAAACATCAGAAGGCTGTAGACAAATACTGGGACAGCTACAACCATC 200
    |  || ||       ||  ||||||  ||  || ||  ||||| ||||| || ||
    CTGGAGACCAGCGAGGGCTGCAGGCAGATCCTGGGCCAGCTGCAGCCCAG

201 CCTTCAGACAGGATCAGAAGAACTTAGATCATTATATAATACAGTAGCAA 250
    |||  |||||| ||       || ||  || ||       |  || ||  || || |||  |
    CCTGCAGACCGGCAGCGAGGAGCTGAGGAGCCTGTACAACACCGTGGCCA

251 CCCTCTATTGTGTGCATCAAAGGATAGAGATAAAAGACACCAAGGAAGCT 300
    ||||  ||  ||  |||||| ||  ||||| ||||| ||  || ||||||||||||  ||
    CCCTGTACTGCGTGCACCAGAGGATCGAGATCAAGGACACCAAGGAGGCC

301 TTAGACAAGATAGAGGAAGAGCAAAACAAAAGTAAGAAAAAAGCACAGCA 350
    |   ||||||||| |||||  |||||  |||||       |||||  ||  || |||||
    CTGGACAAGATCGAGGAGGAGCAGAACAAGTCCAAGAAGAAGGCCCAGCA

351 AGCAGCAGCTGACACAGGACACAGCAGTCAGGTCAGCCAAAATTACCCTA 400
    || || ||  ||||||  ||  ||||||||  |||||  |||||  ||  |||||  |
    GGCCGCCGCCGACACCGGCCACAGCAGCCAGGTGAGCCAGAACTACCCCA

401 TAGTGCAGAACATCCAGGGGCAAATGGTACATCAGGCCATATCACCTAGA 450
    |   |||||||||||||||||||  ||  |||||| ||   |||||||||    || ||
    TCGTGCAGAACATCCAGGGCCAGATGGTGCACCAGGCCATCAGCCCCAGG
```

Fig. 2A

```
451 ACTTTAAATGCATGGGTAAAAGTAGTAGAAGAGAAGGCTTTCAGCCCAGA 500
    ||  | || ||  ||||| || || || || |||||||| |||||||| ||
    ACCCTGAACGCCTGGGTGAAGGTGGTGGAGGAGAAGGCCTTCAGCCCCGA

501 AGTAATACCCATGTTTTCAGCATTATCAGAAGGAGCCACCCCACAAGATT 550
    || || |||||||||    || |    || ||||||||||| || ||
    GGTGATCCCCATGTTCAGCGCCCTGAGCGAGGGAGCCACCCCCAGGACC

551 TAAACACCATGCTAAACACAGTGGGGGGACATCAAGCAGCCATGCAAATG 600
    | |||||||||| |||||  |||||  || || || || ||||||||  |||
    TGAACACCATGCTGAACACCGTGGGCGGCCACCAGGCCGCCATGCAGATG

601 TTAAAAGAGACCATCAATGAGGAAGCTGCAGAATGGGATAGAGTACATCC 650
    | || |||||||||| ||||| || || || || ||||| || || || ||
    CTGAAGGAGACCATCAACGAGGAGGCCGCCGAGTGGGACAGGGTGCACCC

651 AGTGCATGCAGGGCCTATTGCACCAGGCCAGATGAGAGAACCAAGGGGAA 700
    ||||| || || || || || || || |||||||||||| || || | ||| |
    CGTGCACGCCGGCCCCATCGCCCCCGGCCAGATGAGGGAGCCCCGCGGCA

701 GTGACATAGCAGGAACTACTAGTACCCTTCAGGAACAAATAGGATGGATG 750
    | ||||| || || || || || || ||||| ||||| || || || |||||
    GCGACATCGCCGGCACCACCAGCACCCTGCAGGAGCAGATCGGCTGGATG

751 ACAAATAATCCACCTATCCCAGTAGGAGAAATTTATAAAGATGGATAAT 800
    || || || || || ||||| || || |||||| || || || |||||  ||
    ACCAACAACCCCCCCATCCCCGTGGGCGAAATCTACAAGAGGTGGATCAT

801 CCTGGGATTAAATAAAATAGTAAGAATGTATAGCCCTACCAGCATTCTGG 850
    |||||| | || || || || || |||||  |||| |||||| |||||||| ||||
    CCTGGGCCTGAACAAGATCGTGAGGATGTACAGCCCCACCAGCATCCTGG

851 ACATAAGACAAGGACCAAAAGAACCTTTTAGAGACTATGTAGACCGGTTC 900
    | || || ||  || || || |||| || || || |||||| || ||| |||||
    ATATCAGGCAGGGCCCCAAAGAGCCCTTCAGGGACTACGTGGACAGGTTC

901 TATAAAACTCTAAGAGCCGAGCAAGCTTCACAGGAGGTAAAAAATTGGAT 950
    || || || ||  | |||||||| ||         |||||||| || || |||||
    TACAAGACCCTGCGCGCCGAGCAGGCCAGCCAGGAGGTGAAGAACTGGAT

951 GACAGAAACCTTGTTGGTCCAAAATGCGAACCCAGATTGTAAGACTATTT 1000
    ||| || ||| || |||| || || || || ||||| || ||||| ||
    GACCGAGACCCTGCTGGTGCAGAACGCCAACCCCGACTGCAAGACCATCC
```

Fig. 2A

```
1001 TAAAAGCATTGGGACCAGCGGCTACACTAGAAGAAATGATGACAGCATGT 1050
     | || || |||||||| || || || || || || |||||||| || ||
     TGAAGGCCCTGGGACCCGCCGCCACCCTGGAGGAGATGATGACCGCCTGC

1051 CAGGGAGTAGGAGGACCCGGCCATAAGGCAAGAGTTTTGGCTGAAGCAAT 1100
     ||||| || || || ||||||||| ||||| || ||  |||| || || ||
     CAGGGCGTGGGCGGCCCCGGCCACAAGGCCAGGGTGCTGGCCGAGGCCAT

1101 GAGCCAAGTAACAAATACAGCTACCATAATGATGCAGAGAGGCAATTTTA 1150
     |||||| || || || || || |||||| |||||||||||| ||||| || |
     GAGCCAGGTGACCAACACCGCCACCATCATGATGCAGAGGGGCAACTTCA

1151 GGAACCAAAGAAAGATGGTTAAGTGTTTCAATTGTGGCAAAGAAGGGCAC 1200
     |||||| || |||||||| ||||| ||||| || ||||| || || |||
     GGAACCAGAGGAAGATGGTGAAGTGCTTCAACTGCGGCAAGGAGGGCCAC

1201 ACAGCCAGAAATTGCAGGGCCCCTAGGAAAAGGGCTGTTGGAAATGTGG 1250
     || ||||| || ||| | ||||| ||||| |||||||| ||||| || ||
     ACCGCCAGGAACTGCCGCGCCCCAGGAAGAAGGGCTGCTGGAAGTGCGG

1251 AAAGGAAGGACACCCAAATGAAAGATTGTACTGAGAGACAGGCTAATTTTT 1300
     ||||| || ||||| ||||| || || || ||||| ||||| || ||
     CAAGGAGGGCCACCAGATGAAGGACTGCACCGAGAGGCAGGCCAACTTCC

1301 TAGGGAAGATCTGGCCTTCCTACAAGGGAAGGCCAGGGAATTTTCTTCAG 1350
     | || |||||||||||   |||||||||| ||||| || || || || |||
     TGGGCAAGATCTGGCCCAGCTACAAGGGCAGGCCCGGCAACTTCCTGCAG

1351 AGCAGACCAGAGCCAACAGCCCCACCATTTCTTCAGAGCAGACCAGAGCC 1400
     ||||| || |||||| || ||||| || || || |||||||| || |||||
     AGCAGGCCCGAGCCCACCGCCCCCCCCTTCCTGCAGAGCAGGCCCGAGCC

1401 AACAGCCCCACCAGAAGAGAGCTTCAGGTCTGGGGTAGAGACAACAACTC 1450
     || |||||| || || |||||||||||   || || ||||| || || |
     CACCGCCCCCCCCGAGGAGAGCTTCAGGAGCGGCGTGGAGACCACCACCC

1451 CCCCTCAGAAGCAGGAGCCGATAGACAAGGAACTGTATCCTTTAACTTCC 1500
     |||| ||||||||||||||| || ||||||||| ||||| || | || |
     CCCCCCAGAAGCAGGAGCCCATCGACAAGGAGCTGTACCCCCTGACCAGC

1501 CTCAGATCACTCTTTGGCAACGACCCC 1527
     || ||    || || ||||||||||||
     CTGAGGAGCCTGTTCGGCAACGACCCC
```

|   | synthetic | wildtype |   |
|---|---|---|---|
| A | 23.78% | 36.97% | ds DNA |
| T | 10.46% | 18.91% | |
| G | 32.62% | 24.17% | |
| C | 33.14% | 19.95% | |
| A/U | 22,7% | 45,9% | mRNA |
| G/C | 77,3% | 54,1% | |
| CpG | 5 | 1 | |

SYNTHETIC GAGPOL GENES AND THEIR USES

This application claims priority to PCT/EP 01/05744, filed on May 18, 2001, and EP 00 110 623.6, filed May 18, 2000, and is a continuation of U.S. Ser. No. 10/276,482 filed Jun. 19, 2003 now U.S. Pat. No. 7,378,515. The entire text of the above-referenced applications are specifically incorporated herein by reference without disclaimer.

The present invention relates to synthetic gag and gagpol genes optimized for high level expression via codon optimization and the uses thereof for the efficient generation of vector particles. The invention further relates to the generation of packaging cells and vaccines based on the synthetic gag and gagpol genes.

Retroviral based vector particles for gene therapy, retroviral based virus-like particles for vaccination or retroviral based DNA or RNA constructs for DNA vaccination should require the ability to express structural genes and enzymatic functions in high yields in order to obtain maximal efficiency and yet, at the same time, with lowest possible risk and side effects for the recipient. Efficient production of structural or enzymatic proteins from complex retroviruses like HTLV-1 and -2, Lentiviruses and Spumaviruses is limited by their complex regulatory mechanism of transcription, nuclear RNA translocation and expression. For example the expression of SIV and HIV-1 late gene products is highly regulated both on transcriptional and post-transcriptional level therefore depending on the presence and function of early phase proteins like Tat and Rev. Whereas the anti-repressor function of Tat can be easily avoided by using heterologous transcriptional control via viral and/or cellular promotor/enhancer units, the expression of late genes, coding for structural or enzymatic functions (gag, env, pol) depends on the presence of the transactive Rev protein, known to promote the export of un- and partially spliced RNAs from the nucleus to the cytoplasm via the interaction with its cognate RNA recognition site Rev responsive-element (RRE), a complex of a 351 nucleotides (nt) long RNA stem-loop structure located within the env open-reading-frame. Although Rev/RRE action is well accepted as a necessary prerequisite for HIV-1 late gene expression, the critical contribution of different cis-acting elements within the un- and singly spliced transcripts to Rev dependency and timely regulated expression is still controversially discussed. Accordingly, Rev dependent and timely regulated export of late singly or unspliced lentiviral mRNAs has been explained in most reports either by inefficient splice site formation or attributed to inhibitory sequences located within the coding region (referred to as INS elements).

Whereas the exact nature and function of so called INS elements is presently not completely clear, Rev dependent nuclear export and expression of the un- and singly spliced lentiviral mRNAs, at least when expressed from heterologous promoters, seems to engage and require the major splice donor site located in the untranslated region 5' of the Gag coding sequence (5'-UTR). This 5'-UTR also contains part of the RNA packaging signal (ψ), which—in contrast to the ψ-sites of traditional C and D-type retroviruses—also extends into the coding area of lentiviral genomes including the Gag and Pol reading frame.

Although lentiviral vector particles, virus-like particles and DNA or RNA constructs derived from complex retroviruses like HTLV-1 and -2, Lentiviruses and Spumaviruses offer great promise in the field of gene therapy, DNA vaccination and/or vaccination, concerns regarding safety in humans still exist, due to the striking pathogenic potential of HTLV's and lentiviruses like HIV-1 or HIV-2. Moreover, due to the complex viral regulatory mechanisms underlying Gag and GagPol expression efficient expression is either limited by or depends heavily on the presence of cis-acting elements (UTR, RRE) and transactive proteins (Rev, Tat). Tat-independent transcription can be easily achieved by employing a constitutive mammalian promotor like the Cytomegalovirus immediate early promotor/enhancer unit. Rev independent expression of late HIV-1 genes such as those coding for structural or enzymatic proteins would be highly appreciable in order to improve efficiency and safety of lentiviral based gene therapy vector particles and DNA vaccines as well as for antigen production in a mammalian expression system. Generally, two systems can be applied: (a) The Mason-Pfitzer monkey virus (MPMV) constitutive transport element (CTE), a cis-acting RNA element located within the 3' untranslated region (UTR) of the viral genome, can substitute the HIV-1 Rev/RRE regulatory system. In addition, several other cis-acting RNA elements of a variety of viruses also promoting nuclear export of intron containing RNAs were discovered (e.g. Rous sarcoma virus, Simian retrovirus type D, Avian leukemia virus, HBV). Accordingly, the addition of the MPMV-CTE element or functional analogous cis-acting RNA elements overcomes the effect of the so called INS elements, which have been proposed to account for the nuclear sequestration of late lentiviral RNAs in the absence of Rev. (b) Low or no gene expression of late HIV-1 gene products in absence of Rev has been partially overcome by clustered single point mutations within the wobble positions of selected codons within coding DNA sequences (Schwartz et al. 1992a J. Virol. 66:7176-7182; Schneider et al. 1997, J. Virol 71:4892-4903; Haas et al. 1996, Curr. Biol.: 6:315-324). This approach aimed to destroy the so called INS elements in order to render the expression of the resulting Gag gene independent of Rev. However, the presence, nature and function of INS elements is still discussed controversially, indicating that a complete knockout of poorly characterized INS elements on the basis of single point mutations may be difficult to achieve. This view is confirmed by the observation of Qiu and colleagues (Qiu et al. 1999 J Virol. November;73 (11):9145-52.), showing that the addition of a CTE element to the (only partially) altered Gag gene leads to a further increase of Gag expression. This phenomenon does not hold true for a completely Rev-independent Gag expression construct.

A preferred application of HTLV-1 and -2 as well as Lentivirus derived Gag and GagPol based expression constructs is DNA vaccination and the production of antigens, preferably, virus-like particles, in higher eukaryotic expression systems like in mammalian and insect cells. Cell mediated immune responses to Gag and Pol products of HIV-1 were shown to protect from disease or at least to contribute to an efficient control of virus replication. Accordingly, in persons with chronic infection, HIV-1-specific proliferative responses to p24 as well as the number of Gag specific CTL precursors were inversely related to the determined viral loads. Moreover, in CTL responses directed towards highly conserved epitopes within Gag or Pol seem to critically contribute to the control of virus replication in long-term non-progressing HIV infected individuals.

Different formats have been devised in the past towards presenting Gag and Pol containing immunogens to the immune system, recombinant virus-like particles (VLPs) and Gag/Pol containing DNA or RNA constructs being amongst them. VLPs were usually produced in a baculovirus driven insect cell expression system, which allows to bypass the complex regulation of Gag and Pol expression seen in the natural host or mammalian cells. Such VLPs turned out to be highly immunogenic in rodents as well as in nonhuman primates. However, to compile with the regulations of Good Manufacturing Practice (GMP) and in order to achieve proper posttranslational modification of Gag/Pol polypeptides (including coexpressed proteins that might be packaged in or presented by VLPs), expression of GagPol and derivatives thereof in mammalian cell lines would be highly appreciated.

Vaccination by direct injection of DNA is a novel and promising method for delivering specific antigens for immunization. Plasmid DNA immunization has potential advantages compared to traditional protein vaccination due to the strong T helper 1 (Th1) and CTL responses induced, the prolonged antigen expression and the long lived effector activity, and thus can be used for vaccination. In animal models, DNA vaccination has been shown to induce protective immunity against a variety of viral and parasitic pathogens. In most cases, strong, yet highly variable, antibody and cytotoxic T cell responses were associated with control of infection. Plasmid DNAs expressing genes derived from HIV-1 have been recently shown to induce humoral and cellular immune responses in rodents, in nonhuman primates and in phase I studies in humans. Although these constructs were able to induce an immune response, both circulating antibody titers and HIV-1 specific CTL levels were transient and low.

However, the development of DNA or RNA constructs and infectious, although not necessarily replication-competent, bacterial or viral vehicle encoding Gag or GagPol or derivatives for antigen production in eukaryotic cells and for vaccination purposes faces several limitations both, regarding safety and efficiency. Gag and GagPol expression using wildtype genes in the Rev-dependent situation is limited (a) by the complex viral regulatory mechanisms which involves several cis-acting elements (RRE, UTR) and trans-acting proteins (Rev, Tat). In absence of UTR, RRE, or Rev no or only minute amounts of Gag or GagPol protein will be produced. Gag or Gag/Pol expression therefore needs simultaneous expression of the Rev protein either from a bicistronic construct or from a separate plasmid. Both strategies limit the efficiency of generating cell lines in vitro or reduce the efficacy of DNA vaccine constructs in vivo either due to an increase plasmid size or the necessity to transfect/transduce one single cell with both plasmids at the same time; and (b) by the presence of the Rev protein itself, acting as an RNA shuttle between nucleus and therefore harboring an intrinsic risk. Moreover, when applied as a therapeutically vaccination in chronically HIV infected individuals, Rev could contribute towards reactivating latent viruses, thereby enhancing the infection, virus replication and disease.

Moreover, Gag and GagPol expression—irrespective of accomplished by the Rev/RRE system or mediated independent from Rev/RRE by addition of a constitutive transport element (CTE) or analogous cis acting sites—is limited by the presence of UTR, RRE and several stretches in the GagPol coding area, which are known to comprise the HIV-1 packaging signal ψ or other RNA elements responsible for packaging the genomic RNA into viral particles. These gag and gagpol nucleic acids comprising such RNA elements could be packaged into and distributed by endogenous retroviral particles and contribute towards the mobilization of endogenous retroviruses. Additionally, Gag or GagPol derived VLPs generated either in cell culture or in vivo following DNA vaccination would self package their own RNA, which precludes any safe application of such DNA vaccine constructs for vaccination purposes in humans.

Moreover, any kind of Gag and GagPol expression—irrespective of being achieved (i) by Rev/RRE system, (ii) by addition of CTE or analogous sites or (iii) after introduction of single point mutations in the Gag or GagPol gene—is limited by the wildtype sequence itself in the case of a Gag or GagPol DNA vaccine. Recombination events could occur between the vaccine construct itself (UTR, RRE, wildtype ORF) and endogenous retroviral sequences or, when administered as a therapeutic vaccine, between the nucleic acids of the vaccine construct and the genetic information of the virus circulating within the patient. Both could lead to the reconstitution of potentially infectious or chimeric virus particles inheriting unknown risks.

Another preferred application of lentiviral Gag and GagPol based vector particles is gene transfer into different types of dividing, resting or postmitotic cells. In contrast to standard retroviral gene transfer as mediated e.g. by Moloney Murine Leukemia Virus (MoMuLV) based vector particles, lentiviral gene transfer can be used for gene delivery into a variety of quiescent or non-dividing cells, such as neuronal, muscle, and liver as well as hematopoietic stem cells and might therefore considerably contribute to the prevention and treatment of genetic disorders, tumor diseases and infections. The transduction of non-dividing, resting or postmitotic cells as neuronal, hepatical tissue or hematopoietic progenitor cells by for the treatment of variety of genetic disorders or acquired diseases. The lentiviral vector particles are currently prepared by triple-transfection of a GagPol expression plasmid together with a transfer construct (containing the packaging signal and transfer gene; flanked by LTRs), and expression plasmid encoding an envelope protein derived from an amphotropic or xenotropic retrovirus like Moloney Murine Leukemia Virus or Vesicular stomatitis virus into mammalian cell lines. Lentiviral vector particles from the supernatant of such transfected cells were able to stable transduce a large variety of different cells even after in vivo gene transfer. To increase the safety of these vector particles, most of the accessory genes of HIV-1 were deleted from the packaging construct and the vector particles, thereby minimizing the risk for the emergence of potentially pathogenic replication competent recombinants.

However, the development of lentiviral Gag and GagPol based vector particles for gene transfer into quiescent or non-dividing cells faces several limitations regarding safety and efficiency.

The currently used HIV-1 or SIV derived GagPol expression constructs contain parts of the 5'-untranslated region comprising the RNA packaging signal ψ. Although small deletions were introduced into the assumed packaging signal, it is unlikely that these deletions completely prevent packaging, since similar deletions in the context of an intact 5'-leader sequence reduced packaging by less than a factor of 25 (Luban and Goff, 1994 J Virol. June;68(6):3784-93).

Moreover, if the GagPol expression construct can indeed be packaged by homologous or non-homologous recombination events between the viral RNA and the GagPol RNA of the expression construct during or after reverse transcription can not be excluded. This could lead to the—for safety reasons—undesired transfer of the GagPol gene (or parts of it) into target cells.

Moreover, there are two regions of homology between the GagPol expression constructs and the lentiviral transgene constructs: (1) Rev-dependent as well as CTE mediated, Rev independent GagPol expression (packaging proteins) requires either the complete UTR or at least part of it for efficient expression. Also the transgene constructs depend for efficient packaging on the RNA packaging signal that overlaps the 5'-UTR. (2) Since in HIV-1, SIV and other lentiviruses the packaging signal extends from the UTR into the gag gene (reviewed in Swanstrom-R and Wills-J W, 1997, Cold Spring Harbor: Cold Spring Harbor Laboratory Press, pp. 263-334.), the 5'-portion of the gag gene is part of many lentivirus derived transgene constructs. (3) Finally both, the transgene construct and Rev-dependent GagPol expression constructs contain the Rev-responsive element, since (i) RRE was suggested to include RNA packaging functions and (ii) the transport of the transgene RNA and the GagPol RNA from the nucleus to the cytoplasm is Rev-dependent. These regions of extensive homology might facilitate homologous or non homologous recombination events.

The problem underlying the present invention is the development of retroviral based expression constructs allowing high level protein production in absence of transactive proteins and with lowest risk of self packaging of the construct or recombination events thereby avoiding the risk for reconstitution of potentially infectious or by other means hazardous particles. A further problem underlying the present invention is the provision of vaccines against diseases caused by Lentiviruses.

The problem of the invention is solved by the subject matter defined in the claims.

The present invention is further illustrated by the figures.

FIG. 1:

Schematic representation of wildtype and synthetic gag encoding expression constructs. Open boxes indicate wild-type gag (wtgag) encoding genes including 3' and 5' located cis-acting sequences, whereas syngag without any 3' or 5' untranslated regions (UTR) is boxed black. Wtgag reading frames were fused to the cis-acting sequences 5' located UTR, the Rev responsive-element (RRE), the constitutive transport element (CTE), or combination thereof To investigate the influence of the major splice donor (SD) on CTE mediated Rev-independent Gag expression, the UTR were mutated in order to destroy the splice-donor consensus sequence within this upstream located sequence, resulting in mutant ΔSD-wtgag-CTE.

FIG. 2:

Representation of syngag and wildtype gag open reading frames. (A) The synthetic Gag coding sequence (SEQ ID NO: 5) was adapted to a codon usage occurring in highly expressed mammalian genes and aligned to the corresponding wild-type sequence (SEQ ID NO: 10) shown above. Sequence identity between the synthetic and wild-type genes is indicated by lines. (B) The table indicates the different sequence composition of the wildtype and synthetic gag reading frame. The fully synthetic gag gene with an optimized codon usage shows a markedly increase in G/C content whereas the overall A/U content is reduced. Moreover codon usage adaptation increased the amount of immune-stimmulatory CpG islets (Pur-Pur-C-G-Pyr-Pyr) within the coding region from only 1 to 5.

FIG. 3:

H1299 cells were transiently transfected with indicated constructs. For standardization Gag expression was compared to wildtype like Rev/RRE dependent expression mediated by cotransfection of a Rev expression construct (indicated as +). Rev-independent Gag expression was analysed by co-transfection of a negative control construct (vector; indicated as −). (A) Rev/RRE mediated wildtype expression. (B) CTE-mediated wildtype expression. (C) Synthetic expression using a codon optimized reading frame. Cells were harvested 48 hours post-transfection, lysed and 50 μg of total protein subjected to Western Blot analysis (A-C, lower panel). Yields of $Pr55^{gag}$ were measured by testing different dilutions of cell-lysate in a capture-ELISA using purified $Pr55^{gag}$ for standardization (A-C, upper panel) and were normalized by the $Pr55^{gag}$ production obtained by autologous Rev/RRE dependent expression. Gag-expression levels obtained by transfection of different cell lines were performed to rule out cell type specific effects (D). Bars represent relative $Pr55^{gag}$ expression levels (taken UTR-wtgag-RRE+ Rev as 100%) and are given as the mean of triplicate determinations.

FIG. 4:

Immunological analysis of an HIV-1 Gag DNA vaccine based on synthetic and wildtype sequences. 80 μg of wildtype (wt-gag) and synthetic (syngag) encoding DNA expression constructs were injected intramuscularily (im) into BALB/c mice and boosted twice, after 3 weeks and 6 weeks and sacrificed after 7 weeks. (A) Strength of humoral responses induced in immunized BALB/c. Each bar represents the group mean (n=4) for anti-gag IgG1, anti-gag IgG2 and total IgG as determined by end-point dilution ELISA assay. End-point titers of the immune sera were defined as the reciprocal of the highest plasma dilution that resulted in an adsorbance value (OD 492) three times greater than that of a preimmune serum with a cut-off value of 0.05. (B) Cytotoxic T cell activity in splenocytes from mice immunized intramuscularly or subcutaneously by particle gun (p.g.) with gag expression constructs. Lymphoid cells obtained from mice five days after the boost injection were co-cultured with gag peptide-pulsed syngenic P815 mastocytoma cells (irradiated with 20,000 rad). Control assays included splenocytes of non immunized and wt-gag immunized mice stimulated in vitro with peptide-pulsed P815 cells. Cytotoxic effector populations were harvested after 5 days of in vitro culture. The cytotoxic response was read against gag-peptide pulsed A20 cells and untreated A20 negative target cells in a standard $^{51}Cr$ release assay. Data shown were mean values of triplicate cultures.

FIG. 5:

Maps of the (B) SIV-derived packaging constructs based on optimized GagPol reading frames of SIV and HIV and (A) (A) and HIV-1SIV-derived (B) transgene constructs or packaging constructs. Regions deleted from the SIV genome are marked by shaded boxes with the first and last deleted nucleotide given after the "Δ" sign (numbering according to Genbank entry M33262). Point mutations that inactivate reading frames are marked by asterisks, inactivated reading frames are marked in black. Synthetic GagPol reading frames are hatched. BGHpAd: bovine growth hormone polyadenylation signal; CMV: immediate early promoter/enhancer region from human cytomegalovirus; SFFV-Pr: Spleen focus forming virus U3 region; GFP: gene for the green fluorescence protein;

FIG. 6:

Immunoblot analysis of cell culture supernatants harvested 3 days after transfection of H1299 cells with the indicated lentiviral (HIV-1: $Hgp^{syn}$ and $SIV_{mac239}$: $Sgp^{syn}$) GagPol expression constructs and proviral DNAs. Released GagPol particles were enriched by continuous sucrose density gradient sedimentation. Antigen peak fractions were separated on a denaturing 12.5% SDS-PAGE and analyzed by immunobloting using HIV-1 p24 (A) or SIV p27 specific (B) monoclonal antibodies. Protease activity and functionality in the polyprotein processing was shown by absence (−) or presence (+) of Saquinavir. Molecular weights of the detected precursor proteins (Pr) and mature cleavage products are indicated. (C) Additionally, antigen peak fractions were also tested for its content of HIV-1 p24 capsid antigen using a commercially available capture ELISA format (DuPont, Boston, USA)

FIG. 7:

Transduction of growth-arrested cells. 293T cells were transfected with ViGΔBH, pHIT-G and the indicated lentiviral GagPol expression constructs. The MLV vector particle was generated by transfecting plasmids pLEGFP-N1, pHIT60, and pHIT-G. Vector particle titers in the supernatant of transfected cells were determined on 293 cells in the presence of the indicated concentrations of aphidicolin. The titration was done in triplicates or quadruplicates. The means and the standard deviations are shown. GFU: green fluorescence forming units.

FIG. 8:

Detection of replication competent recombinants. CEMx174-SIV-SEAP cells were infected with the supernatant of 293T cells co-transfected with SIV-GFPΔDP (A) or SIV-GFPΔBP (B) and the indicated gag-pol expression constructs. RLU: relative light units.

FIG. 9:

Schematical representation of a codon optimized GagPol derivative which can be used for DNA vaccination. For safety and regulatory reasons the packaging signal Ψ was removed, the integrase deleted, and the reverse transcriptase (RT) gene disrupted by insertion of a scrambled nef gene at the 3'end of the DNA sequence coding for the RT active site. The nef gene was dislocated by fusing its 5'half to its 3'half. Myristilation is of the GagPolNef particles is inhibited by a Glycin to Alanin mutation at the myristilation site of the gag gene.

FIG. 10:

Positioning effect of codon optimized sequences on the level of Gag expression. (A) Representation of the Gag polyprotein (p17, p24, p7 and p6) and the composition of the codon optimized gene encoding Gag. Restriction sites that were introduced for convenient assembly of the codon optimised sequences are shown including their position relative to the ATG (A=1) start codon. The order of the cloned fragments is indicated as F1 to F7 from the amino- to the carboxyterminus of Gag. (B) Composition of chimeric Gag open reading frames. The nomenclature of the synthetic (syn-gag), the wild-type (wt-gag) and the chimeric gag genes (syn1/wt2-7, syn1-2/wt3-7, syn1-3/wt4-7, syn4/wt5-7, wt1-4/syn5-7) are given on the left side. Used abbreviations reflect the composition of the gag genes, respectively, indicating fragments (1 to 7; (A)) that are based either on synthetic (syn-) or wild-type (wt-) sequences. A schematic representation of the gag gene variants is also given (central panel). Closed boxes indicate codon optimised fragments (syn-), open boxes wild-type (wt-) gag coding sequences. Intracellular Gag expression yields measured 2 days following transfection of H1299 cells with the gag gene variants cloned into a pCDNA3.1 vector are indicated at the right. Amounts of synthesized Gag protein were expressed as %p24 compared to p24 levels achieved after transfection of H1299 cells with pCDNAsyn-gag.

The term "vector particle" as used herein refers to a transduction competent viral particle comprising packaging proteins, envelope proteins as exposed on the surface of the viral particle as well as an incorporated transfer construct.

The term "virus-like particle" as used herein refers to a transduction incompetent viral particle comprising at least packaging proteins such as gag or gagpol or derivatives thereof.

The term "construct" as used herein refers to an expression vector in the sense of molecular cloning like a plasmid, bacteriophage, phagemid, phasmids or the like.

The term "packaging construct" as used herein refers to constructs comprising the nucleic acid sequence necessary to produce packaging proteins in eukaryotic cells.

The term "transfer construct" or "gene transfer construct" or "transgene construct" as used herein refers to constructs comprising the nucleic acid sequence necessary to produce an RNA containing the packaging site Ψ, the transfer gene and flanking LTRs or derivatives thereof. This RNA is capable to be incorporated within an transducing viral particle which itself is produced by an eukaryotic cell expressing packaging proteins. The LTRs and the packaging site T is of retroviral, preferably, spumaviral or lentiviral and most preferably, of HIV-1, HIV-2, SIV or FIV origin.

The term "transgene" as used herein refers to a nucleic acid which should be introduced in a cell as a therapeutic agent. This nucleic acid can serve e.g. as a decoy, triplehelix forming or antisense oligonucleotide, as a ribozyme, an aptamere, or as a nucleic acid inserted into the genom in a manner that ensures its function, replication and transmission as a normal gene.

The term "packaging proteins" as used herein refers to GagPol proteins of all retroviruses such as oncoviruses, HTLV-1 and 2, spumaviruses, lentiviruses, e.g. HIV-1, HIV-2, SIV, FIV, and in particular to proteins encoded by SEQ ID NO:2 (GagPol HIV-1$_{IIIB}$) and SEQ ID NO: 1 (GagPol SIV$_{mac239}$), which are capable of packaging an RNA containing the packaging site Ψ such as an retroviral, preferably, lentiviral, most preferably, HIV-1, HIV-2, SIV, FIV genome and/or a transfer construct.

The term "HIV-1$_{IIIB}$" refers to the HIV-1 isolate BH10 (Gen Bank Acc: M15654).

The term "synthetic gag or gagpol" as used herein refers to a complete or a partially codon usage optimized gene, whereas the partially codon optimized portion is located at the 5'-end. Furthermore, the codon optimized portion is strict or fully optimized in a sense that all codons were optimized according to table 1.

The present invention relates to nucleic acid sequences encoding the gag and pol polypeptides, whereby the amino acid Ala is encoded by the nucleic acid triplett gcc or gct, Arg is encoded by agg or aga, Asn is encoded by aac or aat, Asp is encoded by gac or gat, Cys is encoded by tgc or tgt, Gln is encoded by cag or cat, Glu is encoded by gag or gaa, Gly is encoded by ggc or gga, His is encoded by cac or cat, Ile is encoded by atc or att, Leu is encoded by ctg or ctc, Lys is encoded by aag or aat, Met is encoded by atg, Phe is encoded by ttc or ttt, Pro is encoded by ccc or cct, Ser is encoded by age or tcc, Thr is encoded by acc or aca, Trp is encoded by tgg, Tyr is encoded by tac or tat, Val is encoded by gtg ot gtc and the stop codon is tga or taa.

Preferably, the present invention relates to nucleic acid sequences encoding the gag and pol polypeptides, whereby the amino acid Ala is encoded by the nucleic acid triplett gcc or gct, Arg is encoded by agg or aga, Asn is encoded by aac or aat, Asp is encoded by gac or gat, Cys is encoded by tgc or tgt, Gln is encoded by cag or cat, Glu is encoded by gag or gaa, Gly is encoded by ggc or gga, His is encoded by cac or cat, Ile is encoded by atc or att, Leu is encoded by ctg or ctc, Lys is encoded by aag or aat, Met is encoded by atg, Phe is encoded by ttc or ttt, Pro is encoded by ccc or cct, Ser is encoded by age or tcc, Thr is encoded by acc or aca, Trp is encoded by tgg, Tyr is encoded by tac or tat, Val is encoded by gtg ot gtc and the stop codon is tga or taa, whereby the nucleic acid sequence in the region in which the reading frames encoding the gag and pol polypeptides overlap corresponds to the wildtype nucleic acid sequence encoding the gag and pol polypeptides.

Most preferably, the present invention relates to nucleic acid sequences as depicted in SEQ ID NO:1 or 2.

We were able to demonstrate that consequent and strict codon optimization of the Gag and GagPol reading frames derived from lentiviruses, particularly SIV and HIV such as the Simian Immunodeficiency virus SIV$_{mac239}$ and the Human Immunodeficiency virus HIV-1$_{IIIB}$ allowed high level expression of Gag, GagPol and derivatives thereof in complete absence of Rev/RRE, CTE and UTR which can be used directly for DNA vaccination.

Moreover, we were able to demonstrate that consequent and strict codon optimization of lentiviruses, particularly SIV and HIV such as $SIV_{mac239}$ or $HIV-1_{IIIB}$ GagPol reading frames with the exception where Gag and Pol reading frames are overlapping, allowed high level expression of GagPol and derivatives thereof in complete absence of Rev/RRE, CTE and UTR and can be used as packaging constructs for gene delivery.

In addition, we were able to demonstrate that strict and consequent codon usage optimisation of 5' sequences, but not 3' sequences of lentiviral gag genes, particularly those derived from SIV and HIV, e.g. $SIV_{mac239}$ or $HIV-1_{IIIB}$, in particular from nucleotides 1-854, 1-697, 1-489, or 1-294 of the $HIV-1_{HX10}$ gag gene, are sufficient to direct Rev-independent Gag or GagPol expression.

Therefore, safe and efficient delivery and expression of Gag or GagPol genes according to the present invention allows (i) expression of high yields of native proteins in higher eukaryotes like in mammalian or insect cells and (ii) supporting the generation of transduction competent particles for vaccination and gene therapy purposes which is currently limited by the complex regulatory mechanisms of late Gag and GagPol expression.

The present invention is based on the observation, that the codon usage e.g. in the HIV genome (A/T content 55.88%) significantly deviates from that of highly expressed mammalian genes (usually not exceeding 50%) indicating a regulatory function of the codon usage for timely regulated retroviral such as HTLV-1 and -2, oncoviral, spumaviral and lentiviral gene expression.

Additionally, we were able to show that CTE-mediated, similar to the Rev/RRE mediated, expression of wildtype HIV-1 late gene products (such as gag), essentially depends on the presence of the HIV-1 5'-untranslated region (UTR) or at least parts of it, which also contains an RNA stretch responsible for packaging of the genomic RNA into the viral particle, and therefore touches sensible safety issues.

In order to eliminate inhibitory or otherwise regulatory sequences within retroviral such as such as HTLV-1 and -2, oncoviral, spumaviral and lentiviral Gag and GagPol genes, reading frames were optimized according to codon usage found in highly expressed mammalian genes. For that purpose, a matrix was generated considering almost exclusively those codons that are used most frequently and, less preferably, those that are used second most frequently in highly expressed mammalian genes as depicted in table 1. Using these codons from highly expressed human genes a fully synthetic reading frame not occurring in nature was created, which, however encodes the very same product as the original wildtype gene construct.

TABLE 1

Codon most frequently (codon 1) and second most frequently (codon 2) found in highly expressed mammalian genes.

| amino acid | codon 1 | codon 2 |
|---|---|---|
| Ala | GCC | GCT |
| Arg | AGG | AGA |
| Asn | AAC | AAT |
| Asp | GAC | GAT |
| Cys | TGC | TGT |
| End | TGA | TAA |
| Gln | CAG | CAA |
| Glu | GAG | GAA |
| Gly | GGC | GGA |
| His | CAC | CAT |
| Ile | ATC | ATT |
| Leu | CTG | CTC |
| Lys | AAG | AAA |
| Met | ATG | ATG |
| Phe | TTC | TTT |
| Pro | CCC | CCT |
| Ser | AGC | TCC |
| Thr | ACC | ACA |
| Trp | TGG | TGG |
| Tyr | TAC | TAT |
| Val | GTG | GTC |

(Ausubel et al. 1994 Current Protocols in Molecular Biology 2, A1.8-A1.9).

Based on this matrix, the Wisconsin genetics computer group (gcg) software package was employed to create the synthetic reading frame by backtranslating the amino acid sequence of lentiviral Gag and GagPol polypeptides into the codon optimized synthetic reading frame.

Few deviations from strict adherence to the usage of most frequently found codons may be made (i) to accommodate the introduction of unique restriction sites at approximately 250 to 300 nt intervals (see e.g. FIG. 2) (ii) to break G or C stretches extending more than 7 base pairs in order to allow consecutive PCR amplification and sequencing of the synthetic gene product. This may also be performed for the Gag and Pol based expression constructs used for DNA vaccination as well the packaging constructs used for gene transfer with exception of the latter where gag and pol reading frames are overlapping. In particular, it is preferred that the overlapping region of the gag and pol reading frames of the packaging constructs used for gene transfer may not be altered at position 1298-1558 of SEQ ID NO:2 and position 1175-1532 of SEQ ID NO:1, in order to maintain both reading frames.

In particular, the use of the synthetic Gag and Pol genes according to the invention comprising the GagPol genes of all Retroviruses such as Oncoviruses, Human T-cell Leukemia Virus 1 and 2, Spuma- and preferably, Lentiviruses, in particular derived from HIV and SIV as encoded by SEQ ID NO:2 (GagPol $HIV-1_{IIIB}$) and SEQ ID NO:1 (GagPol $SIV_{mac239}$) allows therefore the safe and efficient production of packaging proteins for delivering genetic information to cells, whereas codons of Gag and GagPol reading frames were adapted to highly expressed mammalian genes as specified above, except regions where gag and pol reading frames are overlapping.

Figure 10:
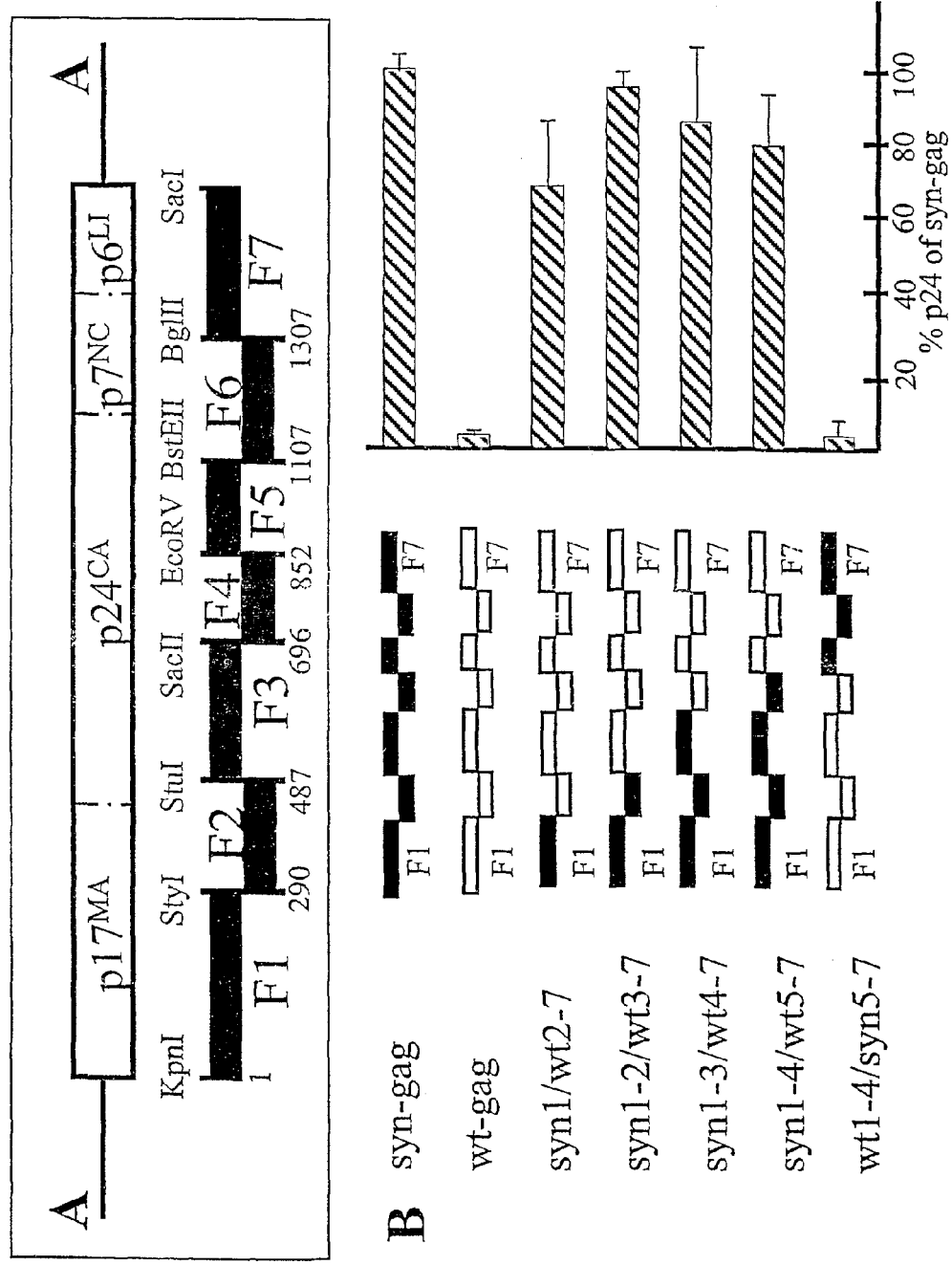

In particular, the use of partially synthetic GagPol genes according to the invention comprising the GagPol genes of all retroviruses such as Oncoviruses, Human T-cell Leucemia Virus 1 and 2, Spuma- and preferably, lentiviruses, in particular HIV and SIV as encoded by chimeric Gag sequences as exemplified in FIG. 10 allows therefore the safe and efficient production of packaging proteins for delivering genetic information into cells, whereas only an N-terminal portion of the GagPol genes were adapted to highly expressed mammalian genes.

The present invention allows therefore the safe and efficient production of packaging proteins by increasing the yields of GagPol synthesis as compared to the expression rates achieved from the wildtype gene or wildtype like genes characterized by clustered point mutations—if driven by the same cellular or viral promotor/enhancer unit—as a result of consequent adaptation of the codon usage to that of frequently expressed mammalian genes.

The present invention allows the safe and efficient production of packaging proteins in complete absence of known cis-acting elements (UTR, RRE) or transactive proteins such as Rev and Tat.

The present invention further relates to a synthetic retroviral gag comprising a 5' sequence with strict and consequent codon usage optimisation and a remaining 3'-sequence having the wildtyp sequence, the codon usage optimisation being sufficient to direct Rev-independent Gag or GagPol expression, wherein the codon optimized 5' region is at least from nucleotide 1 to 150, preferably from 1-294, preferably from 1-489, preferably from 1-697, or preferably from 1-854.

The present invention further relates to retroviral gag or gagpol based vector particles, whereby the packaging proteins are derived from retroviruses and are encoded by nucleic acids according to the invention and the transgene construct is derived from wildtype retroviruses.

The present invention further relates to retroviral gag or gagpol based vector particles, wherein the retrovirus is selected from the group of oncoviruses, HTLV-1 or -2, spumaviruses, lentiviruses, in particular HIV, in particular HIV-1, HIV-1$_{IIIB}$, HIV-2, and SIV, in particular SIV$_{mac239}$.

The present invention further relates to retroviral gag or gagpol based vector particles, whereby the packaging proteins are derived from a first retrovirus and the transgene construct is derived from a different second retrovirus and whereby the packaging proteins are encoded by nucleic acids according to the invention.

The present invention further relates to retroviral gag or gagpol based vector particles, wherein the first and second retrovirus are selected from the group of oncoviruses, HTLV-1 and 2, spumaviruses, lentiviruses, in particular HIV, in particular HIV-1, HIV-1$_{IIIB}$, HIV-2, and SIV, in particular SIV$_{mac239}$.

The present invention further relates to retroviral gag or gagpol based vector particles generated by nucleic acid molecules comprising the nucleic acid sequence according to the invention having at least a 25 fold reduced incorporation rate of said nucleic acid molecules encoding the gag and pol polypeptides compared to retroviral particles generated by wildtype nucleic acid sequences encoding the gag and pol polypeptides.

The present invention further relates to retroviral gag or gagpol based vector particles produced by nucleic acid molecules comprising the nucleic acid sequence according to the invention having at least a 100 fold reduced recombination rate between said nucleic acid molecules encoding the gag and pol polypeptides and a wildtype genome based transgene construct derived from the same or another retrovirus.

The present invention allows the efficient production of safe vector particles by reducing the opportunities for reconstituting infection competent hybrid retroviral particles by recombination events between nucleic acids encoding the packaging proteins and sequences encoding endogenous retroviral particles.

The present invention allows the efficient production of safe vector particles by reducing the risk for incorporating the RNA species encoding the packaging proteins into vector particles by more than 25 fold as compared to expression constructs containing the 5'-UTR or encoding the wildtype GagPol gene or by diminishing the risk of packaging the very same RNA into endogenous retroviral particles.

The present invention allows the efficient production of safe vector particles by reducing the risk of recombination between the packaging construct and the gene transfer construct by more than 100 fold, by combining a synthetic construct encoding the GagPol packaging function from one retrovirus e.g. HTLV-1 and -2, onco-, spuma- or lentivirus with the wildtype genome based transgene construct derived from (i) the very same or (ii) another retrovirus.

Thus, the present invention allows the efficient production of safe vector particles by combining the synthetic gene encoding the packaging proteins derived from a retrovirus, e.g. from lentiviruses, preferably from the HIV-1 or SIV, more preferably from the HIV-1$_{IIIB}$ or SIV$_{mac239}$, with the wildtype transgene construct based on the genome of the same retrovirus, e.g. from lentiviruses, preferably from the HIV-1 or SIV, more preferably from the HIV-1$_{IIIB}$ or SIV$_{mac239}$.

Furthermore, the present invention allows the efficient production of safe vector particles by combining the synthetic gene encoding the packaging proteins derived from a retrovirus, e.g. from lentiviruses, preferably from the HIV-1 or SIV, more preferably from the HIV-1$_{IIIB}$ or SIV$_{mac239}$, with the wildtype transgene construct based on the genome of another retrovirus, e.g. from lentiviruses, preferably from the HIV-1 or SIV, more preferably from the HIV-1$_{IIIB}$ or SIV$_{mac239}$, thereby reducing homologies between transfer vector and packaging vector (as e.g. depicted in table 1 of example 4) resulting in safe and efficient packaging constructs being useful for the production of safe lentiviral vectors and gene delivery systems. Exemplary such vector particles may consist of a synthetic gene encoding the HIV-1$_{IIIB}$ derived packaging proteins with the wildtype SIV$_{mac239}$ genome based transgene construct, or of a synthetic gene encoding the SIV$_{mac239}$ derived packaging proteins with the wildtype HIV-1$_{IIIB}$ genome based transgene construct.

Synthetic GagPol genes may or may not encode the active integrase. In the latter case, the integrase gene may be deleted in total. Alternatively, the enzyme activity may by knocked out by one deletion or several short continuous in frame deletions of various length, preferably, not exceeding 5 amino acids and, more preferably, comprising a single codon. Also, the integrase may be rendered inactive by point mutations at various sites, preferably, by a single point mutation (e.g. position 3930-3932 in SEQ ID No:2 and position 3957-3959 in SEQ ID No:1 are changed to glutamin encoding nucleotides).

The present invention furthermore relates to retroviral packaging cells for the generation of the vector particles according to the invention transformed with nucleic acid molecules comprising the nucleic acid sequence according to the invention.

GagPol packaging proteins according to the present invention may be stably, inducibly or transiently expressed in any primary or lab adapted cell or cell line of human, mammalian or non-mammalian origin. The synthetic GagPol genes may be episomal or chromosomal within these cells and may contain additional recombinant genes, preferable any specific fusogenic gene, more preferable any viral envelope gene, more preferable a retroviral envelope gene. These cells may also contain either an episomal or chromosomal transfer construct, but may not contain any additional viral wildtype sequences.

GagPol expression may be driven by any tissue- or cell type-specific promotor/enhancer such as muscle kreatin kinase or MHC class I promotor/enhancer or by any viral e.g. CMV immediate early, Rous Sarcoma Virus promotor/enhancer, Adenovirus major/late promotor/enhancer or nonviral e.g. synthetic promotor/enhancer.

GagPol expression may be either constitutive or inducible e.g. by addition of a specific inducer like ecdysone in the case of a hormone inducible promotor enhancer or by removal of a repressor protein (Tet on/off) or repressor gene (Cre/Lox).

GagPol based gene delivery into cells may be mediated by any means of transfecting or introducing a plasmid or plasmid derivative such as "midges" (closed linear DNA) encoding the synthetic GagPol gene or the above variants thereof into cells.

GagPol based gene delivery into cells may be also mediated by infectious recombinant (i) viral vectors such as recombinant Retroviruses, Vaccinia- or Poxviruses, Adenoviruses, Alphaviruses, Herpesviruses, Baculoviruses or any other recombinant virus, (ii) subviral components bridging transfection and infection procedures like e.g. Virosomes comprising nucleic acid/protein aggregates containing e.g. Influenca hemagglutinin, (iii) bacterial vectors such as recombinant *Listeriae* or *Salmonellae* or any other type of infectious, replicating or non-replicating vector.

Any means of introducing GagPol genes and derivatives thereof into cells may lead to a transient expression of Gag-Pol. The introduction of the above indicated GagPol genes into cells may also allow the establishment of stable cell lines supporting either constitutive or inducible GagPol expression.

Retroviral, e.g. spumaviral and lentiviral, preferably HIV or SIV derived vector particles carrying the transgene RNA and being capable of transducing nondividing, resting or postmitotic cells of various species in addition to dividing or proliferating cells may be generated by co-expressing a synthetic GagPol constructs according to the invention together with any appropriate amphotropic envelope like the vesticular stomatitis virus G protein, xenotropic envelope like the env protein of avian or murine sarcoma viruses e.g. the Rous sarcoma virus (RSV) Env protein, or cell type specific receptor protein like the HIV-1 Env protein, in the presence of any appropriate gene transfer construct encoding the desired packaging competent transgene RNA.

Transduction competent vector particles may be generated by co-transfecting or co-infecting or transfecting/infecting primary cells or cell lines of various origin such as mammalian Verocells, HeLa, Cos, CHO or H1299 cells or insect SF9, High-5 or DS-2 cells with constructs encoding the synthetic GagPol derived packaging proteins, and any appropriate envelope or receptor structure as well as the desired transgene.

Alternatively, transduction competent vector particles may be generated by stable cell lines expressing GagPol from the synthetic GagPol gene according to the invention, either inducible or constitutively, whereby the stable cell lines may be co-transfected or co-infected or transfected/infected with constructs encoding any envelope or receptor structure as well as the desired transgene.

Preferably, transduction competent vector particles may be generated by stable cell lines expressing GagPol from the synthetic GagPol gene according to the invention together with any appropriate envelope or receptor structure, either inducible or constitutively, whereby the stable cell lines may be transfected or infected with constructs encoding the desired transgene.

Ideally, transduction competent vector particles may be obtained from a stable cell line mediating the expression of the synthetic GagPol gene and any appropriate receptor or envelope function together with the generation of the packaging competent transgene RNA, either in an inducible manner or constitutively or a combination thereof.

Most preferably, transduction competent vector particles are generated by transfection of cells with a plasmid or derivative thereof or by infecting cells with any infectious, although not necessarily replication competent, bacterial or viral vehicle encoding the synGagPol derived packaging proteins, and any appropriate envelope or receptor structure as well as the desired transgene.

Both transduction competent vector particles, as well as infectious, although not necessarily replication competent, bacterial or viral vehicle encoding the synGagPol derived packaging proteins, and any appropriate envelope or receptor structure as well as the desired transgene may be used for application ex vivo and in vivo.

Furthermore, the present invention relates to nucleic acid molecules comprising the nucleic acid sequence according to the invention for use as an active pharmaceutical substance.

The present invention relates further to the use of nucleic acid molecules comprising the nucleic acid sequence according to the invention for the preparation of a pharmaceutical composition for the treatment and prophylactic of diseases caused by retroviruses.

Moreover, the present invention can be used for vaccination purposes, in particular, if used as nucleic acid based vaccination constructs, which have been shown to elicit a strong humoral and Th-1 like cellular immune response in mice. On the basis of the GagPol genes of the present invention it is now possible to construct effective retroviral, e.g. HTLV-1 and -2, lentiviral, e.g. comprising all known HIV and SIV clades and sequences as well as derivatives, preferably HIV-1$_{IIIB}$ or SIV$_{mac239}$, based Gag and GagPol vaccines, thereby increasing the yields of GagPol production by the use of either fully or, as exemplified in FIG. 10, partially codon optimized GagPol genes or derivatives thereof as compared to the expression rates achieved from the wildtype gene or wildtype like genes characterized by clustered point mutations—if driven by the same cellular or viral promotor/enhancer unit—as a result of consequent adaptation of the codon usage to that of frequently expressed mammalian genes.

A preferred object of the present invention is the construction of retroviral GagPol based vaccines e.g. oncoviral, spumaviral or lentiviral, preferably HIV and SIV, more preferably HIV-1$_{IIIB}$ or SIV$_{mac239}$ based vaccines, especially modified also to improve safety of GagPol derived candidate vaccines if delivered e.g. as a DNA or RNA vaccine, by any kind of infectious, replicating or non replicating bacterial or viral vehicle or if administered as GagPol derived virus-like particles by consequent and strict codon usage adaptation in complete absence of known cis-acting elements or transactive proteins such as Rev and Tat.

Another preferred object of the present invention is the construction of retroviral GagPol based vaccines by reducing the opportunities for reconstituting infection competent hybrid retroviral particles by recombination events between nucleic acids encoding the packaging proteins and sequences encoding endogenous retroviruses.

Another preferred object of the present invention is the construction of GagPol based vaccines by reducing the risk for incorporating the RNA species encoding Gag, GagPol or derivatives thereof into subviral Gag or GagPol derived virus-like particles by more than 25 fold as compared to expression constructs containing the 5'-UTR or encoding the wildtype Gag and GagPol derived genes and by diminishing the risk of packaging the very same RNA into endogenous retroviral particles thereby reducing the risk of recombination between the nucleic acid derived from a vaccine construct encoding Gag, GagPol or derivatives thereof according to the present invention with DNA or RNA derived from an infection by HIV, SIV or any lenti- or retrovirus or otherwise related virus.

This results in safe and efficient DNA or RNA constructs being useful for the production and delivery of safe GagPol derived vaccine constructs.

The present invention further relates to the nucleic acid sequence as depicted in SEQ ID NO:4.

The present invention further relates to nucleic acid molecules according to the invention, comprising an amino acid substitution wherein the myristilation of the gag-precursor is inhibited.

The present invention further relates to nucleic acid molecules according to the invention, wherein the HIV or SIV N-terminal amino acid glycin is substituted to alanin.

The present invention further relates to nucleic acid molecules according to the invention, wherein one nucleotide is added or two nucleotides are deleted to introduce a ribosomal frameshift so that the gag and pol coding regions are using the same reading frame.

The present invention further relates to nucleic acid molecules according to the invention, comprising a deletion of the complete protease gene or of a part of the protease gene or one or more point mutations in the protease gene so that the protease is rendered inactive.

The present invention further relates to nucleic acid molecules according to the invention, comprising a deletion of the complete reverse transcriptase gene or of a part of the reverse transcriptase gene or one or more point mutations in the reverse transcriptase gene so that the reverse transcriptase is rendered inactive.

The present invention further relates to nucleic acid molecules according to the invention, comprising a deletion of the complete integrase gene or of a part of the integrase gene or one or more point mutations in the integrase gene so that the integrase is rendered inactive.

In order to further increase the safety of the vaccine constructs, codon optimized Gag or GagPol genes may be modified at distinct sites.

Preferably, the Gag or GagPol based synthetic gene is modified in such a way that the myristilation of Gag-precursors is inhibited (e.g. position 4-6 in SEQ ID No:2 and position 4-6 in SEQ ID No:1 are changed to alanin or valin encoding nucleotides), thereby preventing budding of Gag or GagPol derived virus-like particles and increasing the amount of endogenously produced antigen.

Preferably, the Gag or GagPol based synthetic gene is modified in such a way that the Gag and Pol coding regions are using the same reading frame by introducing a ribosomal frameshift, e.g. by either introducing one nucleotide or deleting two nucleotides at any position, without creating a premature stop codon within the Gag coding region, preferably, between the position of the natural frameshift target site (slippery sequence; corresponding to position 1297 SEQ ID No:1 and position 1294 SEQ ID No:2) and the Gag stop codon (specified by SEQ ID No:3), thereby increasing the amount of synthesized pol gene products.

Preferably, the Gag or GagPol based synthetic gene is modified in such a way that the protease (PR) activity is rendered inactive by a deletion comprising the complete or part of the PR gene or by one or several short continuous in frame deletions of various length, preferably, not exceeding 5 amino acids and more preferably, comprising a single codon, most preferably, encoding the aspartic acid at the PR active site. Also, the PR may be rendered inactive by point mutations at various sites, preferably, by a single point mutation any position, most preferably, at the active site (e.g. position 1632-1635 in SEQ ID No:2 and position 1575-1577 in SEQ ID No:1 are changed to asparagin or alanin encoding nucleotides).

Preferably, the Gag or GagPol based synthetic gene is modified in such a way that the active site of the reverse transcriptase gene (RT) is rendered inactive by a deletion comprising the complete or part of the RT gene or one or several short continuous in frame deletions of various length, preferably, not exceeding 5 amino acids and more preferably, comprising a single codon encoding an amino acid at any position, most preferable within the active site being critical for RT function. Also, the RT may be rendered inactive by point mutations at various sites, preferably, by a single point mutation at the active site (e.g. position 2349-2351 in SEQ ID No:2 and position 2136-2138 in SEQ ID No:1 are changed to asparagin or glutamic acid encoding nucleotides).

Preferably, the Gag or GagPol based synthetic gene is modified in such a way that the active site of the reverse transcriptase gene (RT) is dislocated e.g. at the very C-terminus of the synthetic GagPol gene in order to inhibit polymerase activity thereby preventing the production of potentially hazardous nucleotide sequences and/or reconstitution of infectious or by other means hazardous virus particles.

Preferably, the Gag or GagPol based synthetic reading frame is modified in such a way that the other lentiviral genes such as nef, rev, tat, which are rendered biological inactive (e.g. by gene scrambling), are inserted into selected parts of the Gag or GagPol reading frames, Preferably, into the active site of RT in order to broaden immunogenicity and safety.

Preferably, the Gag or GagPol based synthetic gene is modified in such a way that the potentially hazardous genes, like the integrase (IN) are deleted. Alternatively, the enzyme activity may by knocked out by one deletion or several short continuous in frame deletions of various length, preferably, not exceeding 5 amino acids and more preferably, comprising a single codon. Also, the integrase may be rendered inactive by point mutations at various sites, preferably, by a single point mutation (e.g. position 3930-3932 in SEQ ID No:2 and position 3957-3959 in SEQ ID No:1 are changed to glutamin encoding nucleotides).

Figure 9:
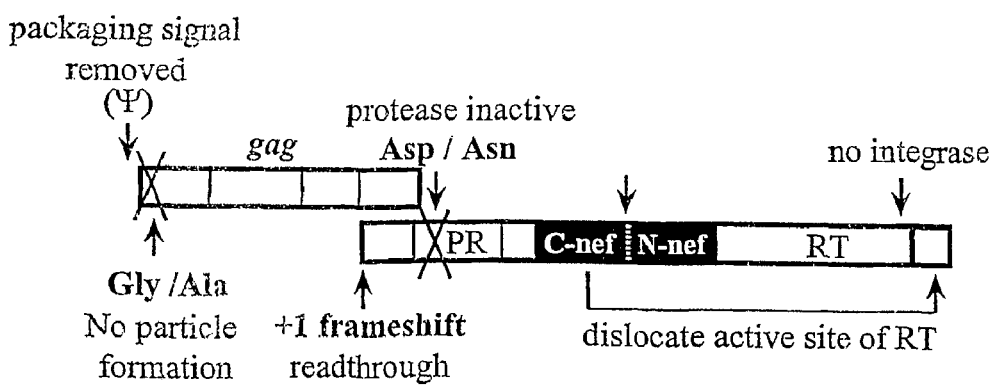

Alternatively, the Gag or GagPol based synthetic gene is modified by any combination of the above described possibilities. An example of a derivative of a HIV-1$_{IIIB}$ GagPol based construct modified as described above, is depicted in FIG. 9 and specified in SEQ ID No:4. The myristilation defective GagPol based derivative is at least as immunogen as the corresponding myristilation competent GagPol based derivative.

Strict adherence to the codon usage of highly expressed mammalian genes also leads to an increase of the overall GC, GG and CC content and thereby introduces potentially immunomodulatory nucleic acid motifs that increase humoral and cellular immune responses at least 2-fold as compared to the corresponding wildtype gene or wildtype like genes that were rendered partially Rev independent by clustered point mutations.

The GagPol product or derivatives thereof encoded by the gagpol genes of the present invention may be stably, inducibly or transiently expressed in any primary or lab adapted cell or cell line of human, mammalian or non-mammalian origin in order to produce GagPol antigens, GagPol containing virus-like particles or derivatives thereof.

The expression of codon optimized GagPol or derivatives thereof in cell culture as well as in vivo following immunization with DNA or RNA constructs specified below may be driven by any tissue- or celltype-specific cellular promotor/enhancer such as muscle kreatin kinase or MHC class I promotor/enhancer or by any viral (e.g. CMV immediate early;

Rous Sarcoma Virus promotor/enhancer, Adenovirus major/late promotor/enhancer) or nonviral e.g. synthetic promotor/enhancer.

GagPol expression may be either constitutive or inducible e.g. by addition of a specific inducer such as ecdysone in the case of a hormone inducible promotor enhancer or by removal of a repressor (Tet on/off) or repressor gene (Cre/Lox).

The delivery of codon optimized GagPol genes or derivatives thereof into cells in vitro may be mediated by any means of transfecting or introducing a construct, e.g. a plasmid or plasmid derivative such as "midges" (closed linear DNA) encoding the synthetic GagPol gene or the above variants thereof into cells.

The delivery of codon optimized GagPol genes or derivatives in vivo may be mediated by injection of the construct, construct derivative or infectious, replicating or nonreplicating bacterial or viral vehicle into any site, preferably, intramascularly, subcutaneously or intradermally, co-administered with any kind of adjuvant e.g. liposomes, ISCOMS, alum or via biodegradable particles, either directly or using technical devices like particle gun, biojector or by any other means.

The delivery of codon optimized GagPol genes or derivatives into cells in vitro and in vivo may be also mediated by infectious or non infectious recombinant viral vehicles such as recombinant Retroviruses, Vaccinia- or Poxviruses, Adenoviruses, Alphaviruses, Herpesviruses, Baculoviruses or any other recombinant virus, subviral components bridging transfection and infection procedures like e.g. Virosomes comprising nucleic acid/protein aggregates containing e.g. Influenza hemagglutinin, or bacterial vectors such as recombinant *Listeriae* or *Salmonellae* or any other type of infectious, replicating or non-replicating vector.

EXAMPLE 1

Construction of the synthetic gag gene. All subsequent numbering of HIV-1 wildtype nucleotide sequences correspond to the HIV-1 isolate BH10 (GenBank Accession: M15654). All subsequent numbering of synthetic HIV-1 Gag encoding reading frames correspond to the start codon of the respective coding region. Position of restriction sites are defined by their cleavage site.

Figures 2B, 3A:
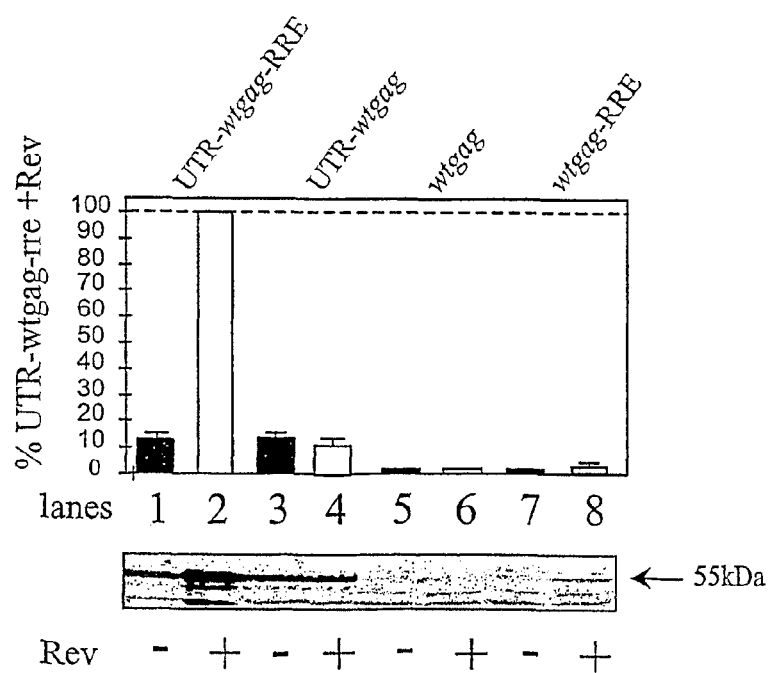

In order to eliminate inhibitory sequences within the HIV-1 gag reading frame, a synthetic gene was constructed, as described above, encoding the entire Pr55$^{gag}$ polyprotein via a codon-usage occurring most frequently in highly expressed mammalian genes. Few deviations from strict adherence to the optimized codon usage were made to accommodate the introduction of unique restriction sites at approximately 250 to 300 nt intervals (Seq ID No: 5). A comparison of synthetic and wildtype Gag coding sequences is shown in FIG. 2 A demonstrating that almost every wobble position within the wildtype coding region was altered by construction of the synthetic gene. The Wisconsin genetics computer group (gcg) software package was used to compare the varying composition of the wildtype and synthetic gag reading frame. Codon optimization resulted in an increased G/C and decreased A/U (T) content, as well as in a 5 fold increase in immune stimulatory CpG motifs (FIG. 2B).

A synthetic sequence coding for the HIV-1$_{IIIB}$ Pr55$^{gag}$ polyprotein was generated by translating the amino-acid sequence of the gag coding region (nucleotides 112-1650) into a synthetic-gag (syngag) coding sequence using a codon-usage occurring most frequently in mammalian cells as depicted in Seq ID No: 5. In order to fragmentize the syngag reading-frame, unique restriction sites were generated at positions 5 (NarI), 290 (StyI), 487 (StuI), 696 (SacII), 852 (EcoRV), 1107 (BstEII) and 1307 (BglII) by silent mutations. For cloning, additional restriction sites KpnI (95), BamHI, XhoI and SacI were introduced within non-coding regions. Synthetic fragments spanning regions between restriction sites KpnI/StyI (F1), StyI/StuI (F2), StuI/EcoRV (F3), EcoRV/BstEII (F4), BstEII/BglII (F5) and BglI/SacI (F6) were created by stepwise PCR-amplification with overlapping 60 nt long oligonucleotides and subcloned using the pCR-Script™ Amp SK(+) Cloning Kit (Stratagene, Heidelberg, Germany) following the manufactures instructions. The unique restriction sites KpnI, StyI, StuI, EcoRV, BstEII, SauI and SacI were used to assemble the fragments into a complete reading frame. Finally, full-length syngag was placed into the KpnI and XhoI restriction sites of of pcDNA3.1 (+) expression vector (Invitrogen, Leek, The Netherlands) under the transcriptional control of the immediate-early promoter-enhancer of the Cytomegalovirus (CMV) allowing constitutive transcription in mammalian cells.

Construction of chimeric Gag genes. Chimeric Gag genes were generated based on the synthetic HIV-1$_{IIIB}$ derived synthetic gag-gene cloned into pCRscript Amp plasmid. Thus, different fragments of the synthetic gag-gene were replaced by wild type gag-sequences. For that purpose, wild type gag sequences corresponding to the codon optimised gag fragments that have been used to assemble the synthetic gag gene were amplified from an HX10 template using primer pairs that included restriction sites flanking the synthetic gene fragments, respectively (FIG. 10A, F1-F7). The chimeric Gag constructs shown in FIG. 10 were subcloned into a pcDNA 3.1+ expression vector.

Several wildtype expression vectors were established by means of standard molecular biology techniques in order to compare expression of synthetic and wildtype gag reading frames. Subgenomic HIV-1 wildtype sequences were cloned by PCR amplification or restriction digestion of HX10 provirus DNA (Ratner et al. 1987, AIDS Res. Hum. Retroviruses. 1987. 3:57-69). The wildtype gag sequence (nucleotides 9-1640) including a 5'-located 103 bp long UTR was cloned into the KpnI and XhoI restriction sites of pcDNA3.1 (Stratagene) expression vector after PCR amplification of a 1667 nt fragment with primers utr-1 (5'-gcg ggt acc gaa ttc cga cgc agg act cgg ctt gc-3') and gag-2 (5'-gcc gag ctc ctc gag gga tcc tta ttg tga cga ggg gtc gtt gcc aaa gag-3') resulting in pCMV-UTR-wtgag. Wildtype gag was cloned into the KpnI and XhoI restriction sites of pcDNA3.1 (Stratagene) expression vector by PCR amplification of a 1537 nt fragment (103-1640) with primers gag-1 (5'-gcg ggt acc gaa ttc agg aga gag atg ggt gcg aga gcg tca gta tta agc-3') and gag-2 resulting in pCMV-wtgag. PCR amplification of the UTR with primers utr-1 and utr-2 (5'-gga tgg cgc cca tct ctc tcc ttc tag cct cc-3') resulted in a 103 nt fragment (9-112) which was cloned into the KpnI and NarI restriction sites of pCMV-syngag, thereby placing the UTR directly 5' of the start-codon of syngag resulting in pCMV-UTR-syngag. BglII and BamHI digestion of HX10 proviral DNA released a 854 nt fragment (6976-7830) containing the RRE and an inefficiently used splice acceptor site (pos. 7734). This RRE containing fragment was cloned into the BamHI restriction site of the plasmids pCMV-UTR-wtgag, pCMV-wtgag, and pCMV-UTR-syngag resulting in pCMV-UTR-wtgag-RRE, pCMV-wtgag-RRE and pCMV-UTR-syngag-RRE, respectively. A DNA fragment coding for the constitutive transport element (CTE) RNA element of Simian Mason-Pfizer D-type retrovirus (MPMV, Accession Nr. M12349, nucleotides 7886 to: 8386), was amplified using MPMV proviral DNA as template and primers cte-1 (5' gct aGG ATC Ccc att atc atc gcc tgg aac 3') and cte-2 (5' cga aCT CGA Gca aac aga ggc caa gac atc 3'). The 500 bp fragment was cloned into the BamHI and XhoI restriction sites of pCMV-wtgag and pCMV-UTR-wtgag resulting in constructs pCMV-wtgag-CTE and pCMV-UTR-wtgag-CTE respectively. A schematic representation of all constructs is summarised in FIG. 1A.

EXAMPLE 2

Transfection of Gag encoding expression constructs into mammalian cells. Cells were transfected by the calcium coprecipitation technique (Graham and Van der EB 1973, Virol. 52, 456-467). The day prior to transfection 2×10⁶ cells were plated on 100 mm-diameter culture dishes and incubated for 24 hours. For transfection, 30 µg of Pr55gag expressing plasmids was used and the total amount of DNA adjusted to 45 µg with either pcDNA3.1(+) vector or for co-transfection experiments with pCMV-rev. Cells were harvested 48 hours post transfection, washed two times in PBS and then further analyzed. Western blot analysis of cells transfected with Gag encoding expression constructs. Harvested cells were lysed in 0.5% Triton X-100, 100 mM Tris/HCl (pH7.4) subjected to repeated freeze/thaw cycles, cleared by centrifugation (20800×g for 5 min.) and the total amount of protein measured by BIO-RAD Protein-Assay (Bio-Rad Laboratories, Munich, Germany) following the manufactures instructions. 50 µg total protein were separated by electrophoresis on a denaturing SDS 12.5% polyacrylamide gel and transferred onto nitrocellulose membrane by electroblotting. Expression of $Pr55^{gag}$ was detected by a HIV-1 p24 specific monoclonal antibody 13-5 (Wolf et al. 1990, AIFO 1:24-29) and visualized by chromogenic staining.

Gag capture-ELISA of cells transfected with Gag encoding expression constructs. The p24 capture-ELISA antibodies were kindly provided by Dr. Matthias Niedrig (RKI, Berlin, Germany). 96-well MaxiSorp ELISA plates (Nunc, Wiesbaden, Germany) were coated over night a with 100 µl of p24-specific monoclonal antibody 11-G-7 diluted 1:170 with 0.1 M carbonat-buffer (pH 9.5). The plates were washed 6 times with wash-buffer (0.1% Tween 20, 300 mM NaCl, 10 mM $Na_2HPO_4$ $2H_2O$, 1.5 mM $NaH_2PO_4$ $H_2O$). Different amounts of cell-lysats were diluted in 0.5% BSA in wash-buffer added to the wells and incubated over night at 4° C. with a second horse-radish-peroxidase conjugated monoclonal antibody (diluted 1:600 in 0.5% BSA in wash-buffer), recognizing a different epitope within p24. After washing the plates 6 times with wash-buffer, antibody conjugates were stained with OPD-solution (Abbott, Wiesbaden, Germany) and absorption OD (495 nm) measured with an ELISA Reader. The concentration of $Pr55^{gag}$ was determined by a calibration curve using different concentrations of purified $Pr55^{gag}$, produced in insect cells using the baculovirus expression system (Wagner et al. 1994, Virology 200:162-175).

As expected, synthesis of $Pr55^{gag}$ from the wildtype gag gene (wtgag) was extremely low in absence of RRE and Rev (FIG. 3 A, lanes 5,6). However, following fusion of RRE downstream of wtgag gene and co-transfection of Rev, $Pr55^{gag}$ production increased only by factor of 1.5-2, suggesting that the Rev/RRE system per se was not sufficient to promote substantial Gag expression (FIG. 3A, lanes 7, 8). In contrast, addition of the authentic 103 bp UTR 5' to the gag gene resulted in a 4-5 fold increase in protein production even in the absence of Rev (FIG. 3A, lane 1, 3 and 4). Additionally, Rev/RRE interaction led to a further increase in $Pr55^{gag}$ production by a factor of 5-8 (2-4 ng/µg total protein; FIG. 3 A, lane 2) and by several orders of magnitude compared to wtgag-RRE co-transfected with Rev. Substitution of Rev/RRE by CTE-mediated nuclear export depended in very same way on the presence of the authentic UTR resulting on high level Gag expression. However, CTE mediated $Pr55^{gag}$ production (FIG. 3B, lane 3) reached only 70% -80% (1.3-1.6 ng/µg total protein) of the Rev-dependent Gag expression using Rev/RRE. (FIG. 3B, lane 1), whereas in absence of UTR or only very little Gag was produced (FIG. 3B, lanes 4, 5).

Figure 3B:
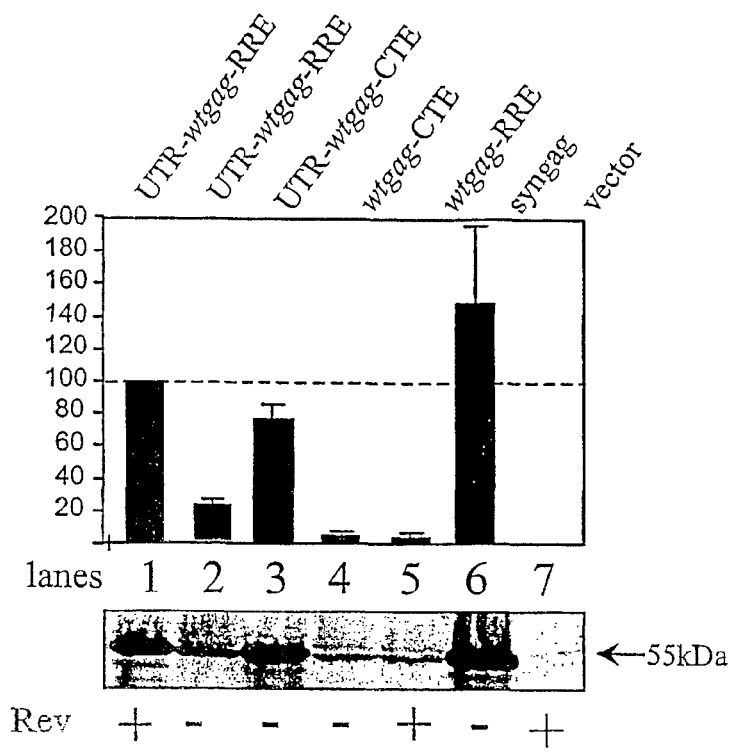
Figure 3C:
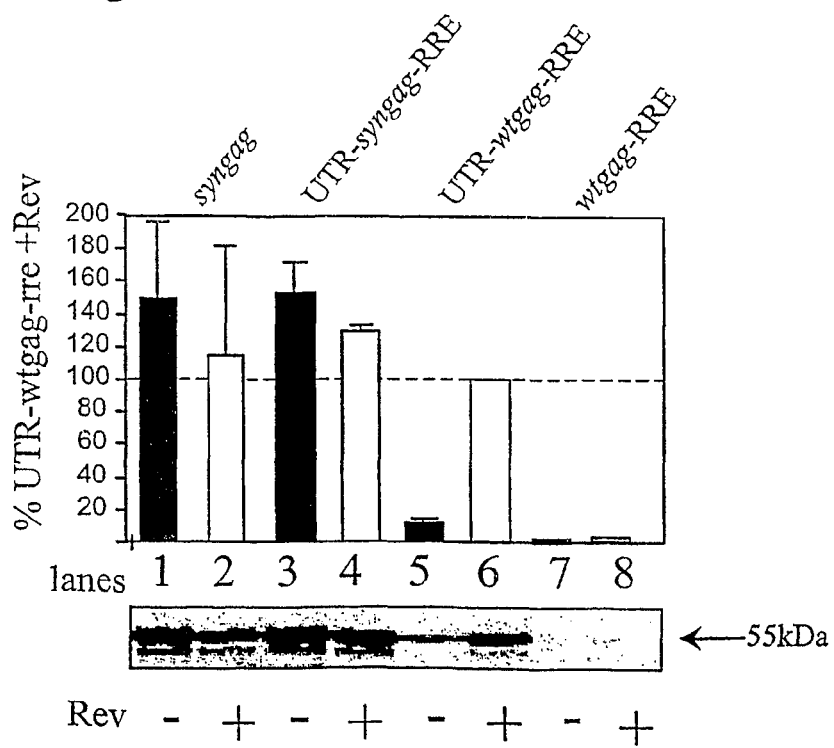

High level expression of $Pr55^{gag}$ was achieved in all cases after transient transfection of the syngag encoding plasmids (FIG. 3C lane 1-4). Expression levels were not substantially altered by introducing the Rev/RRE system and was neither dependent nor influenced by the presence of UTR (FIG. 3C lanes 3-4). $Pr55^{gag}$ expression levels exceeded those accomplished by CTE-mediated wtgag expression by more than 130%, and by about 50% to 100% by co-transfection of UTR-wtgag-RRE with Rev (FIG. 3C, lane 6) and by orders of magnitude to those accomplished by wtgag-RRE whether or not Rev was co-transfected (FIG. 3C, lane 7, 8). Therefore, codon usage adaptation allows Rev-independent expression in absence of any cis-acting regulatory elements resulting in high yields of $Pr55^{gag}$ production (3.5-6.5 ng/µg total protein).

Figure 3D:
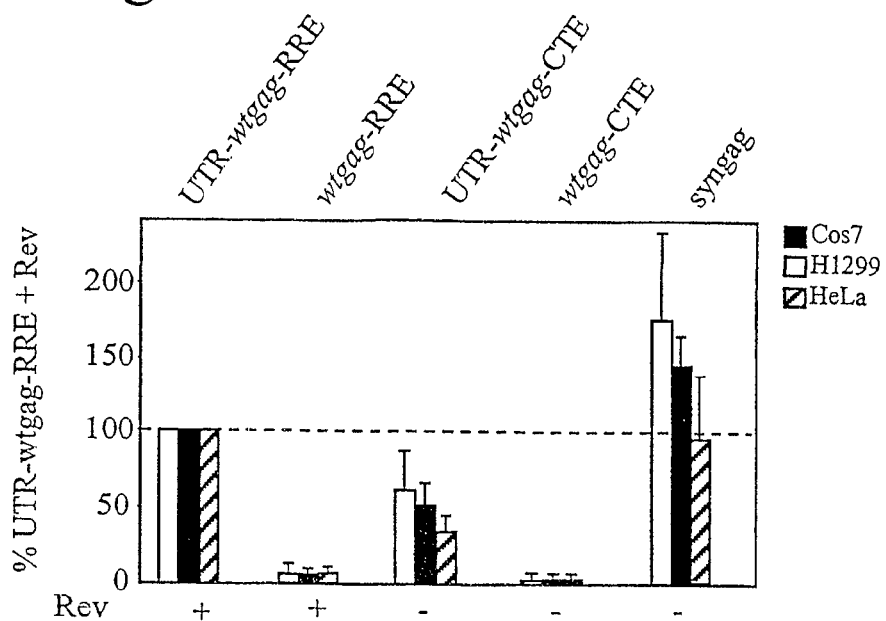

These results were confirmed using various cell-lines (Cos7, HeLa) ruling out that cell-type specific factors critically contributed to the observed effects (FIG. 3D).

Noteworthy, as indicated in FIG. 10, substitution of nucleotides 1-294 in the wild-type Gag gene by a strictly codon optimised synthetic gag sequence was sufficient to support substantial, Rev-independent Gag expression. This effect was even more pronounced, when the codon optimised fragment was extended to the 5' 489, 697 or 845 nucleotides. However, reversing the order of codon optimised and wild type sequences starting with 854 wild-type gag nucleotides followed by codon optimised gag-sequences resulted in a reduction of Gag expression to almost background levels. This strongly suggests that positioning strictly and consequently codon optimised gag sequences to the 5'- but not to the 3'-end of the Gag gene clearly accounts for increased and Rev-independent Gag-expression.

EXAMPLE 3

Immunogenicity of Gag expression vectors after naked DNA vaccination. Female BALB/c mice (Charles River, Sulzfeld, Germany) were housed under specific pathogen-free conditions and injected at the age of 6 to 12 weeks. In order to evaluate the efficiency and type of immune response induced by either wildtype or synthetic reading frames after DNA vaccination, groups of each 3 mice received a subcutaneous (s.c.) primary injection, at the base of the tail, of a solution containing 100 µg plasmid DNA in a total volume of 100 µl PBS. At week 3 and 6 after the primary injection, mice received a boost injection, respectively.

Serum was recovered from mice by tail bleed at week two after the boost injection. Antibodies specific for the HIV $Pr55^{gag}$ polyprotein were quantified by an end-point dilution ELISA assay (in duplicate) on samples from individual animals. In brief, a solid phase of PrepCell purified Pr55gag proteins (100 µl of 1 µg/ml per well, overnight at 4° C. in a refrigerator) was used to capture $Pr55^{gag}$-reactive antibodies from the serum (2 h at 37° C.), which were then detected with horseradish peroxidase (HRP)-conjugated goat anti-mouse IgG1, IgG2a and total IgG antibodies (1:2000 in PBS, 2% Tween 20, 3% FCS; 100 µl/well; PharMingen, Hamburg, Germany), followed by o-phenlyenediamine dihydrochloride solution (100 µl/well, 20 min at room temperature in the dark; Abbott Laboratories, Abbott Park, Ill.). End-point titers were defined at the highest serum dilution that resulted in an adsorbance value (OD 492) three times greater than that of the same dilution of a nonimmune serum. The serum of each mouse was assayed and these values were used to calculate the mean and standard deviation for each group of five mice. Single cell suspensions were aseptically prepared from spleens of mice 5 days after the boost immunization. Cells were suspended in α-MEM medium (Gibco) supplemented with 10 mM HEPES buffer, $5\times10^{-5}$ β-mercaptoethanole and 10% FCS. 5% of a selected batch of Con A-stimulated rat spleen cell supernatants (Poggi et al. 1994, Eur J Immunol. 1994 Sep;24(9): 2258-61) were further added to the culture medium as a source of growth factors. Responder cells ($3\times10^7$) were cocultured with $1.5\times10^6$ syngenic, $V3_{LAI}$ peptide-pulsed P815 cells (irradiated with 20,000 rad) in 10 ml tissue culture medium in upright 25 cm$^3$ tissue culture flasks in a humidified atmosphere with 7% $CO_2$ at 37° C. Cytotoxic effector populations were harvested after 6 days of in vitro culture. Serial dilutions of effector cells were cultured with $2\times10^3$ target cells in 200 µl round-bottom wells. Targets were autologous A20 cells ($2\times10^4$/ml) incubated overnight at 37° C. with $10^{-8}$ M of a 18-mer $V3_{LAI}$ peptide or a 23-mer $p24CA_{LAI}$ peptide. Non peptide-pulsed cells were used as a negative control. Target and control A20 cells were labeled with $^{51}$Cr (1 hour at 37° C., 20 µCi/$10^6$ cells) prior to being added to the effector cells. After a 4 hour incubation at 37° C., 100 µl of supernatant were collected for γ-counting. The percentage specific release was calculated as [(experimental release-spontaneous release)/(total release-spontaneous release)]×100. Total counts were measured after adding 1% Triton X-100 to the labeled target cells. Spontaneously released counts were always less than 20% of the total counts. Data shown are the mean of triplicate cultures. Standard errors of the mean of triplicate data were always less than 20% of the mean.

Figure 4B:
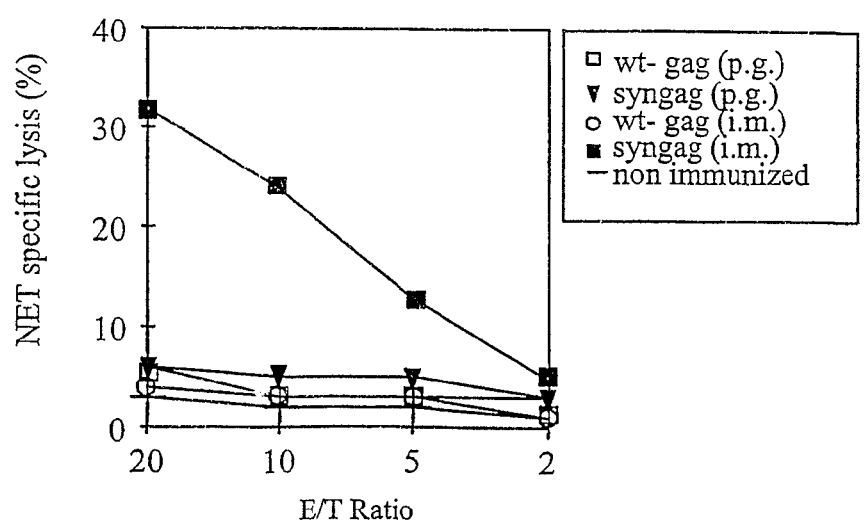
Figure 4A:
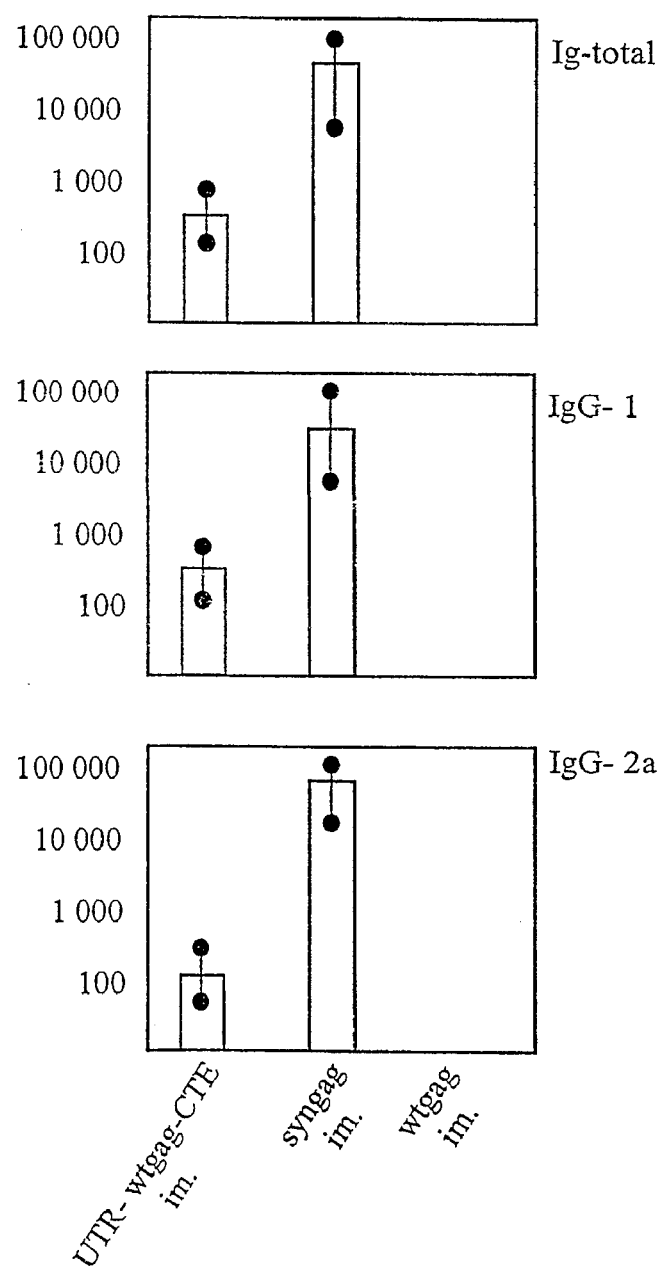
Figure 5A:
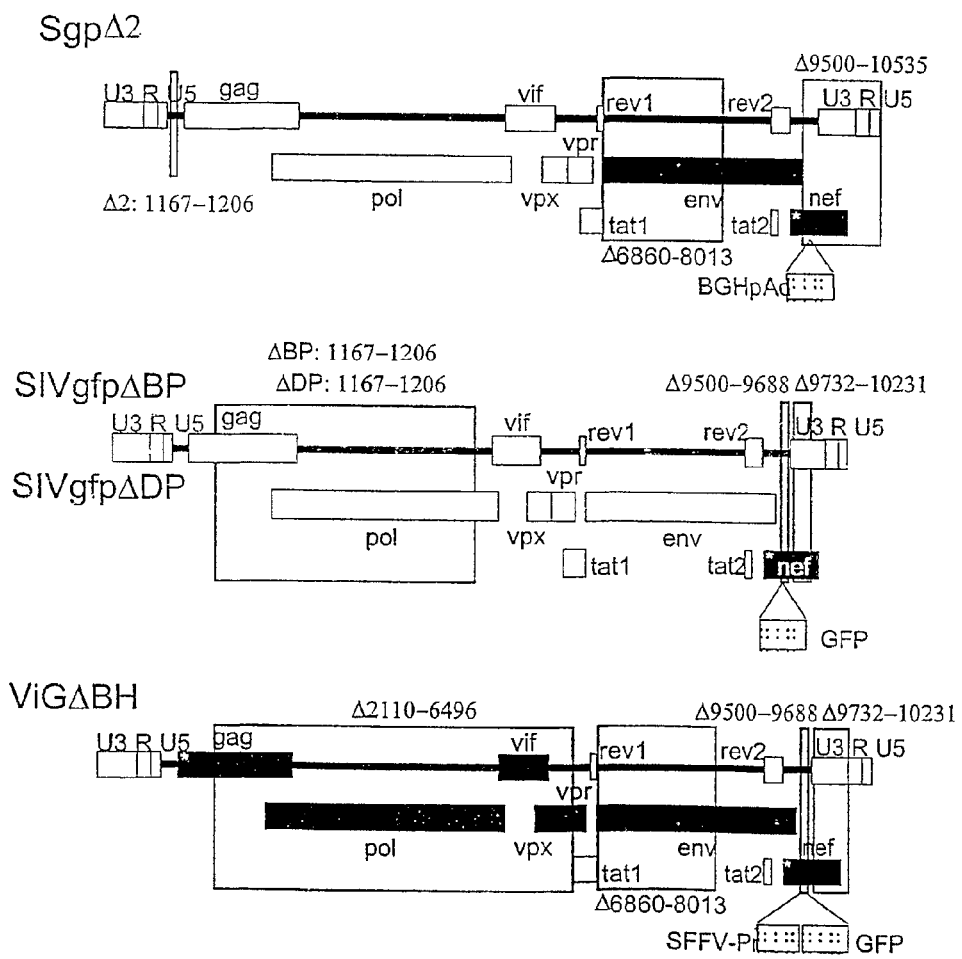
Figure 5B:
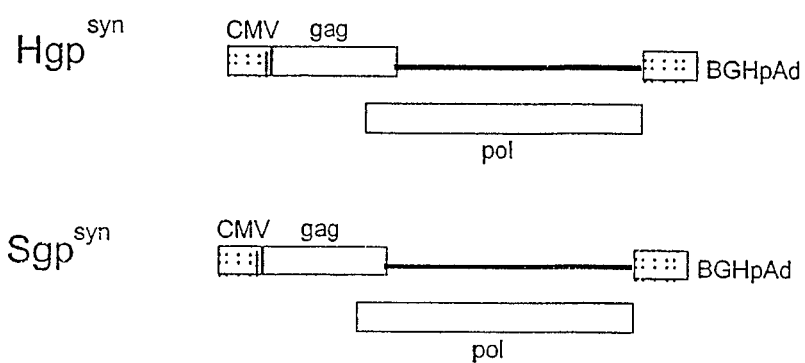

As depicted in FIG. 4, synthetic genes derived from lentiviral pathogens are capable of inducing a strong humoral and cellular immune response. Only in mice immunized with synthetic gag plasmids high levels of specific antibodies could be detected. A Th-1 response induces more likely a cellular immune response, which was verified by CTL chromium release assay of freshly prepared spleen cells of the immunized mice. Again, only mice immunized with a Gag expression plasmid encoded with an optimized codon usage was capable of inducing a strong cytolytic activity and therefore cell mediated immune response.

EXAMPLE 4

Construction of synthetic genes coding for packaging functions of a lentiviral gene transfer vector system. All subsequent numbering of nucleotide sequences referring to synthetic GagPol sequences of HIV-1 or SIV correspond to the start codon of the respective coding region. Position of restriction sites are defined by their cleavage site.

Design of a codon optimized HIV-1 GagPol gene encoding packaging functions. A synthetic sequence coding for the HIV-1$_{IIIB}$ (BH10, GenBank Accession: M15654) Pr160$^{GagPol}$ polyprotein was generated by backtranslating the amino-acid sequence of the GagPol coding region (nucleotides 1-4343), except for the region where gag and pol reading frames are overlapping (nucleotides 1298-1539), and by using a codon-usage occurring most frequently in mammalian cells (as depicted in Seq ID No:2). In order to fragmentize this synthetic GagPol reading-frame ($Hgp^{syn}$), restriction sites were introduced at positions 290 (StyI), 487 (StuI), 1056 (PflMI), 1107 (BstEII), 1549 (BalI), 1852 (SauI), 2175 (AccI), 2479 (BstXI), 2682 (EcoNI), 2867 (SphI), 3191 (PflMI), 3370 (BclI), 3588 (BalI), 3791 (XmaIII), and 4105 (StyI) by silent mutations. For cloning, additional restriction sites KpnI, XhoI and SacI were introduced within non-coding regions. Synthetic fragments spanning regions between restriction sites KpnI/StyI (F1), StyI/StuI (F2), StuI/BstEII (F3), BstEII/BalI (F4), BalI/SauI (F5), SauI/AccI (F6), AccI/BstXI (F7), BstXI/EcoNI (F8), EcoNI/SphI (F9), SphI/PflMI (F10), PfiMI/BclI (F11), BclI/BalI (F12) BalI/XmaIII (F13), XmaIII/StyI (F15) and StyI/SacI (F16) were created by a stepwise PCR-amplification of overlapping 60 nt long oligonucleotides and subcloned using the pCR-Script™ Amp SK(+) Cloning Kit (Stratagene, Heidelberg, Germany) following the manufactures instructions. The unique restriction sites KpnI, StyI, Stul, BstEII, and SacI were used to assemble the fragments F1 to F4 into one intermediate fragment (F1-4). The unique restriction sites KpnI, BalI, SauI and SacI were used to assemble the fragments F5 to F7 into a second intermediate fragment (F5-7). The unique restriction sites KpnI, BstXI, EcoNI, SphI, PflMI, BclI, BalI, XmaIII, StyI and SacI were used to assemble the fragments F8 to F16 into a third intermediate fragment (F8-16). The intermediate fragments (F1-4, F5-7 and pF8-16) were finally assembled into the full-length synthetic GagPol reading frame using restriction sites KpnI/BstEII, BstEII/AccI, and AccI/SacI respectively, and placed into the KpnI and SacI restriction sites of the pCR-Script™ Amp SK(+) cloning vector (Stratagene, Heidelberg, Germany). In order to obtain high level, constitutive expression in mammalian cells the synthetic GagPol coding region was placed into the KpnI and XhoI restriction sites of pcDNA3.1(+) expression vector (Invitrogen, Leek, The Netherlands) under the transcriptional control of the immediate-early promoter-enhancer of the Cytomegalovirus (CMV) resulting in plasmid $Hgp^{syn}$ (encoding HIV-1 GagPol). Design of a codon optimized SIV GagPol gene encoding packaging functions. A synthetic A synthetic sequence coding for the $SIV_{mac239}$ (SIVmm239, GenBank Accession: M33262) $Pr160^{GagPol}$ polyprotein was generated by backtranslating the amino-acid sequence of the GagPol coding region (nucleotides 1-4358), except the region where gag and pol reading frames are overlapping (nucleotides 1299-1533), and by using a codon-usage occurring most frequently in mammalian cells. In order to fragmentize this synthetic SIV derived GagPol reading frame, restriction sites were introduced at positions 120 (BstXI), 387 (XmaIII), 650 (PstI), 888 (NdeI), 1224 (ApaI), 1422 (NspI), 1583 (EheI), 1899 (SauI), 2019 (BsaBI), 2372 (EcoNI), 2651 (SacII), 2785 (BclI), 3025 (BamHI), 3268 (StyI), 3573 (BalI), 3745 (SauI), 3923 (PflMI), and 4188 (ApaI) by silent mutations. For cloning, additional restriction sites KpnI, XhoI and SacI were introduced within non-coding regions. Synthetic fragments spanning regions between restriction sites KpnI/BstXI (F1), BstXI/XmaIII (F2), XmaIII/PstI (F3), PstI/NdeI (F4), NdeI/ApaI (F5), ApaI/NspI (F6), NspI/EheI (F7), EheI/SauI (F8), SauI/BsaBI (F9), BsaBI/EcoNI (F10), EcoNI/SacII (F11), SacII/BclI (F12), BclI/BamHI (F13), BamHI/StyI (F14), StyI/BalI (F15), BalI/SauI (F16), SauI/PflMI (F17), PflMI/ApaI (F18) and ApaI/SacI (F19) were created by a stepwise PCR-amplification of overlapping 60 nt long oligonucleotides and subcloned using the pCR-Script™ Amp SK(+) Cloning Kit (Stratagene, Heidelberg, Germany) following the manufactures instructions. The unique restriction sites KpnI, BstXI, XmaIII, PstI, NdeI, ApaI and SacI were used to assemble the fragments f1 to f6 into one intermediate fragments (f1-6). The fragments f7 to f11 were assembled into a second intermediate fragment (f7-11) using the unique restriction sites KpnI, EheI, SauI, BsaBI, EcoNI and SacI. The unique restriction sites KpnI, BclI, BamHI, StyI, BalI, SauI, PflMI, ApaI and SacI were used to assemble the fragments f12 to f19 into a third intermediate fragment (f12-19). The intermediate fragments f1-6, f7-11 and f12-19 were finally assembled into the full-length synthetic GagPol gene of SIV using restriction sites KpnI/NspI, NspI/SacII, and SacII/SacI respectively, and placed into the KpnI and SacI restriction sites of the pCR-Script Amp SK(+) cloning vector (Stratagene, Heidelberg, Germany). In order to obtain high level, constitutive expression in mammalian cells the SIV derived synthetic GagPol gene was placed into the KpnI and XhoI restriction sites of pcDNA3.1 (+) expression vector (Invitrogen, Leek, The Netherlands) under the transcriptional control of the immediate-early promoter-enhancer of the Cytomegalovirus (CMV) resulting in plasmid $Sgp^{syn}$ (encoding $SIV_{mac239}$ GagPol).

Codon usage of the 4.3 kb long GagPol genes of HIV-1 and SIV was optimized for expression in human cells by assembling the entire reading frame from synthetic oligonucleotides. The synthetic genes encode GagPol proteins which have the same amino acid sequence as wildtype SIV or HIV-1 GagPol. On the nucleotide level there is an overall identity of 69.27% for the synthetic and wildtype GagPol of HIV-1 and of 73.24% for the synthetic and wildtype SIV GagPol genes (Table 1).

TABLE 1

Genetic distances between the different SIV and HIV-1 GagPol coding sequences

| GagPol gene | $SIV^{syn}$ | $SIV^{wt}$ | $HIV^{syn}$ | $HIV^{wt}$ |
|---|---|---|---|---|
| $SIV^{syn}$ | 0.00 | 29.81 | 36.16 | 72.21 |
| $SIV^{wt}$ | — | 0.00 | 69.78 | 54.72 |
| $HIV^{syn}$ | — | | 0.00 | 30.73 |
| $HIV^{wt}$ | — | — | — | 0.00 |

Distance matrix of $SIV_{mac239}$ and $HIV_{IIIB}$ derived synthetic (syn) and wildtype (wt) GagPol coding sequences. Numbers indicate the percentage of missmatches between the compared GagPol sequences.

Optimizing the codon usage of HIV-1 GagPol reduces the homology to wildtype SIV GagPol by 41.48% and vice versa (Table 1). The longest stretch of nucleotide identity between synthetic and wildtype GagPol is 357 bp in SIV and 306 bp in HIV-1. This stretch is located in the $p6^{gag}/p6^{pol}$ overlap region containing the slippery sequence and a stem loop structure, both of which are required for proper ribosomal frameshifting.

EXAMPLE 5

Expression of synthetic GagPol genes. Rev-independent expression of the synthetic HIV-1 and SIV GagPol genes was assayed in transient transfection experiments followed by characterisation of the GagPol particles by conventional immunoblot analysis. Briefly, the day prior to transfection $2\times10^6$ H1299 cells were plated on 100 mm-diameter culture dishes and incubated for 24 hours. Cells were transfected using 45 μg of the synthetic GagPol expressing plasmids or proviral DNA (HX10 and $SIV_{mac239}$) with the calcium phosphate coprecipitation method as described (Graham and Van der EB 1973, Virol. 52, 456-467). Cell culture supernatants were harvested 72 hours post transfection. To block processing of GagPol, plated cells were cultured and transfected in the presence of 10 μM Saquinavir. GagPol particles were purified by separating the culture supernatants on 10-60% sucrose gradients as previously described (Wagner et al. 1994, Virology 200:162-175). GagPol particles banded at the expected density of 1.13 to 1.19 g/cm$^2$, typical for HIV virions. The fractions with highest particle content were dialized against PBS and further separated by electrophoresis on a denaturing SDS 12.5% polyacrylamide gel prior to transfere onto nitrocellulose membrane by electroblotting. HIV-1 p24 capsid (CA) and SIV p27 CA and their precursor proteins were detected by the monoclonal antibodies 13-5 (Wolf et al. 1990, AIFO 1:24-29.) and 55-2F12 (NIH, Rockville, USA), respectively.

Western Blot analyses from supernatants of cells transfected with expression plasmids for the synthetic HIV-1 and SIV GagPol genes ($Hgp^{syn}$, $Sgp^{syn}$ in FIG. 5 B) revealed efficient expression of GagPol in the absence of Rev (FIGS. 5A, B). The GagPol levels obtained with the synthetic genes were significantly higher as the levels obtained by transfection of infectious proviral constructs in the presence of Rev as assessed by a commercial capture ELISA format. Subviral particles were readily released from cells transfected with the synthetic GagPol expression plasmids and sedimentate at a density of about 1.16 g/ml, comparable to wildtype SIV or HIV-1 virions. No differences were observed in the processing of the GagPol precursor proteins encoded by the wildtype viruses and the corresponding synthetic GagPol genes (FIGS. 5A, B).

EXAMPLE 6

Vector production and infection of target cells. The 293T cells were transfected with the calcium phosphate coprecipitation method as described (Graham and Van der EB 1973, Virol. 52, 456-467). The plasmids pHIT60 (MLV GagPol expression plasmid), pHIT-G (VSV-G expression plasmid), SgpΔ2 (SIV-GagPol expression plasmid also expressing vif, vpr, vpx, tat and rev), and ViGΔBH (self-inactivating SIV vector expressing the green fluorescent protein gene (GFP) under the control of the promoter and enhancer from spleen focus forming virus) have been described previously (Graham and Van der EB 1973, Virol. 52, 456-467; Fouchier et al. 1997, EMBO 16, 4531-4539). The Murine leukemia virus (MLV) vector pLEGFP-N1, which contains the GFP gene under the control of an internal CMV promoter, was obtained from Clontech. The supernatant of the transfected cells was passed through a 0.45 μm filter and stored in aliquots at −80° C. The vector stocks were assayed for CA antigen levels using an HIV p24 enzyme-linked immunosorbent assay (ELISA) kit (Innogenetics, Gent, Belgium). The standard included in the ELISA kit was used for quantification of HIV-1 p24 CA antigen levels. Recombinant SIV p28 CA antigen from the SIV p28 antigen capture assay from the AIDS vaccine program (NCI-Frederic cancer research and development center) served as a standard for the quantification of SIV p28 levels.

To determine vector titers, 293 cells were seeded at $2.5\times10^4$ cells per well of a 24-well plate. One day later, the medium was removed and cells were incubated for 2 to 4 hours with serial dilutions of the vector preparations in a total volume of 200 μl. Fresh medium was added and the number of GFP positive cells was determined two days after infection. To arrest 293 cells in the G1/S phase of the cell cycle, cells were seeded in a 96-well plate at a density of 2 to $5\times10^4$ cells per well at a concentration of 1, 3, or 5 μg aphidicolin/ml (Sigma). The titer of the vector stocks was determined on these cells as described above with aphidicolin being present during the entire culture period.

Figure 6A:
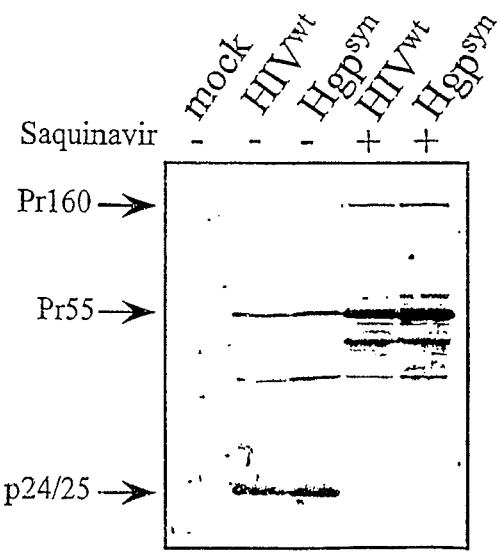
Figure 6B:
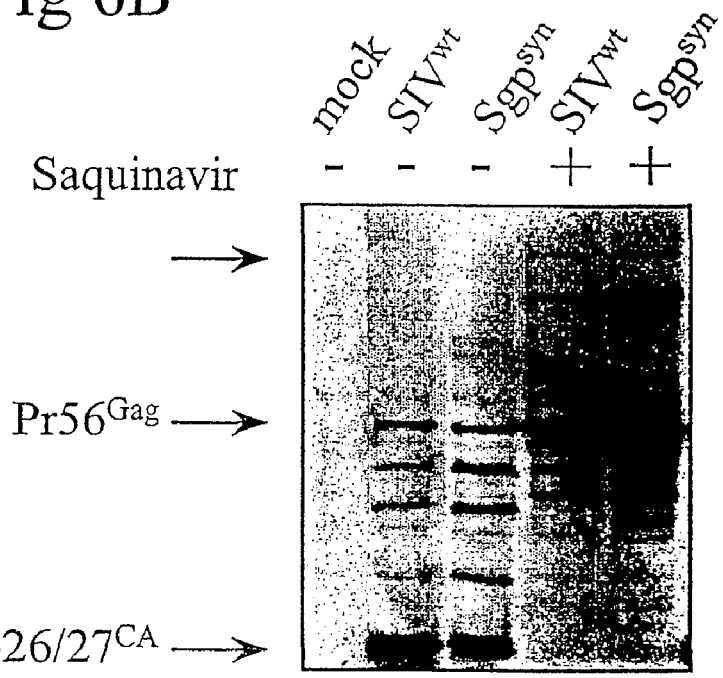
Figure 6C:
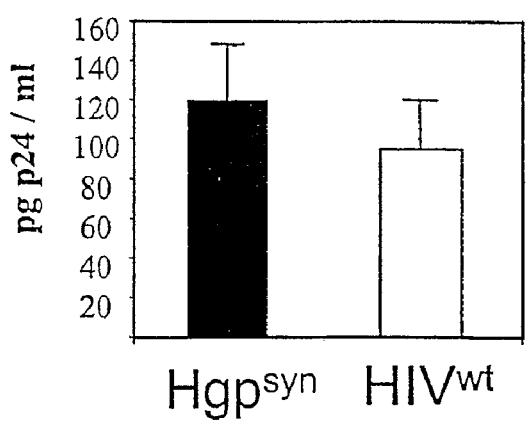

The functional integrity of the GagPol proteins being encoded by synthetic genes was analysed by cotransfection of the synthetic GagPol expression plasmids and an expression plasmid for VSV-G (pHIT-G) with the SIV vector ViGΔBH (FIG. 6). This is a self-inactivating vector, which expresses the green fluorescent protein gene (GFP) under the control of an internal promoter. The vector titers in the supernatant of the transfected cells were in the range of 1×10⁶ GFP-forming units/ml supernatant (Table 2). Similar titers were obtained after cotransfection of ViGΔBH with a wildtype GagPol expression plasmid of SIV (SgpΔ2). The synthetic HIV-1 GagPol expression plasmid also allowed efficient transfer of the SIV vector (Table 2). The infectivity of the vector particles varied less than 2-fold between the different GagPol expression plasmids used (Table 2). Therefore, HIV-1 GagPol must recognise all cis-acting sequences of SIV required for packaging, reverse transcription, and integration with similar efficiency as SIV. As using packaging functions the results clearly extent a previous report on the packaging of HIV-2 RNA, which is closely related to SIVmac, in HIV-1 particles (Kaye and Lever, 1998, J.Virol. 72, 5877-5885).

TABLE 2

Titer and infectivity of an SIV vector packaged by synthetic SIV and HIV-1 GagPol expression plasmids

| Plasmids transfected | Titer$^a$ | | Infectivity$^b$ |
| --- | --- | --- | --- |
| | Experiment 1 | Experiment 2 | |
| SgpΔ2, ViGΔBH, VSV-G | $5.0 \times 10^6$ | $1.4 \times 10^6$ | $5.9 \times 10^5$ |
| Sgp$^{syn}$, ViGΔBH, VSV-G | $1.0 \times 10^6$ | $2.7 \times 10^5$ | $3.4 \times 10^5$ |
| Hgp$^{syn}$, ViGΔBH, VSV-G | $2.0 \times 10^6$ | $2.0 \times 10^6$ | $3.1 \times 10^5$ |
| ViGΔBH, VSV-G | <5 | <5 | n.a. |

$^a$GFP forming units (GFU) per ml supernatant of 293T cells transfected with the indicated plasmids;
$^b$GFU/ng CA antigen in the supernatant of transfected 293T cells;
n.a.: not applicable.

Figure 7:
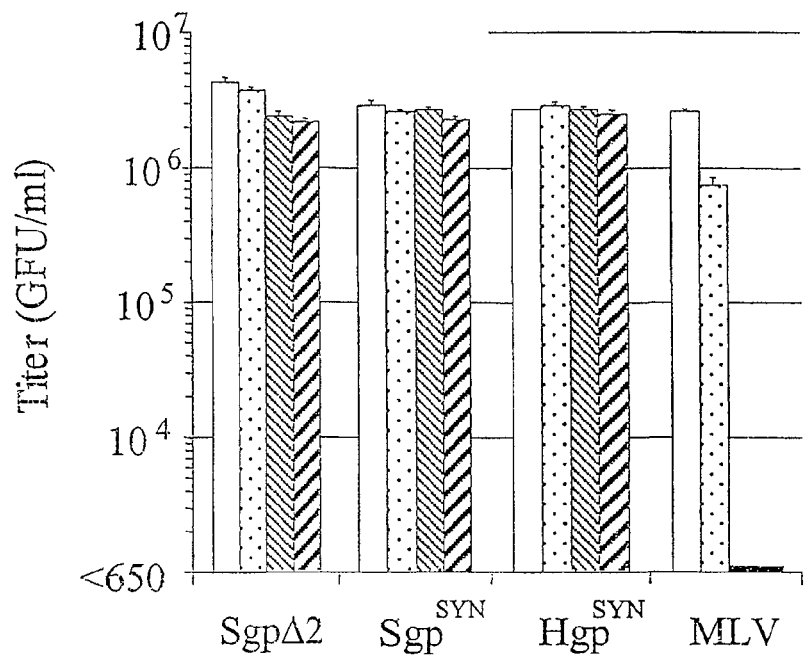

Omitting the GagPol expression plasmid reduced the titer below the level of detection (Table 2), which argues against VSV-G mediated pseudotransduction. In addition, the percentage of GFP positive cells transduced with ViGΔBH, which had been packaged by Sgp$^{syn}$, Hgp$^{syn}$, or SgpΔ2, did not decrease significantly during a six week observation period (data not shown), which suggests integration of the vector into the host genome. As previously observed for another SIV vector packaged by SgpΔ2 and pHIT-G replication competent recombinants could not be detected during an 8 week observation period in ViGΔBH vector preparations packaged by SgpΔ2, Sgp$^{syn}$, or Hgp$^{syn}$ and pHIT-G (data not shown). The transduction efficiency of vectors produced with the synthetic GagPol genes for non-dividing cells was assessed by arresting the target cells in the G1 phase of the cell cycle by aphidicolin treatment. The titer of an MLV-based vector in growth-arrested cells was reduced to background levels (FIG. 7). In contrast, the SIV vector titer was only slightly reduced by aphidicolin treatment. Non-dividing cells could be transduced with the SIV vector independent of the GagPol expression plasmid used for the production of the vector particle (FIG. 7).

EXAMPLE 7

CEMx174 cells (5×10⁵) were infected for 4 hours with 0.5 ml of the vector preparation. The cells were washed three times with PBS and subsequently cultured in 5 ml medium. Infected cultures were split 1:5 to 1:10 twice weekly for eight weeks. The capsid antigen levels in theses cultures were determined 1 and 4 days, and 2, 4, 6 and 8 weeks after infection using the HIV-Innogenetics ELISA and the recombinant SIV p28 antigen as a standard. To determine the emergence of RCR on CEMx174-SIV-SEAP cells (Means et al., 1997, J.Virol. 71, 7895-7902), 1×10⁵ cells were infected with 1 ml supernatant of the transfected cells for two hours and washed once in PBS. Infected cultures were cultured in 5 ml medium and split 1:5 to 1:10 twice weekly for four weeks. Secreted alkaline phosphatase activity in the supernatant of these cultures was determined at different time points after infection with the Phospha-Light-kit (Tropix, Bedford, Mass., USA) as described by the manufacturer. The titer of RCRs was determined by limiting dilution. CEMx174-SIV-SEAP cells (2×10⁵) were incubated with 1 ml supernatant in a final volume of 2 ml. After two hours, six 200 µl aliquots were transferred to a 96-well plate and used as a starting point for 4-fold serial dilutions. Cultures were split 1:10 after one week. Syncytia formation was scored 1 and 2 weeks after infection and the TCID$_{50}$ of the RCRs was calculated as described (Johnson and Byington, 1990, Quantitative assays for virus infectivity. In Techniques in HIV research. A. Aldovini and B. D. Walker, eds. (New York: Stockton Press), pp. 71-76. 1990).

Figure 8A:
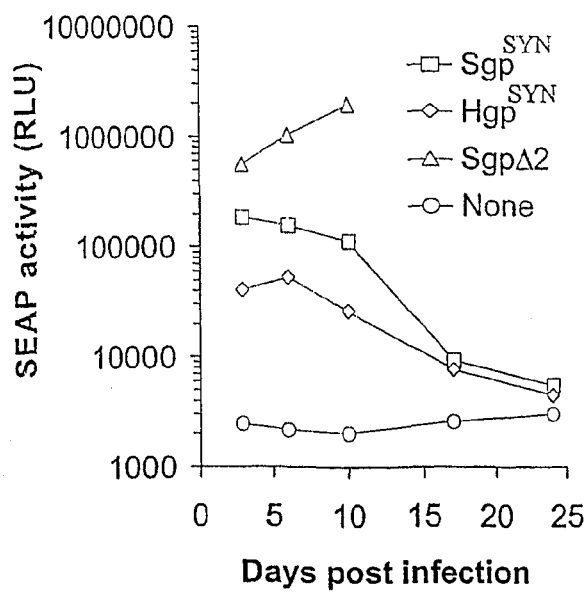
Figure 8B:
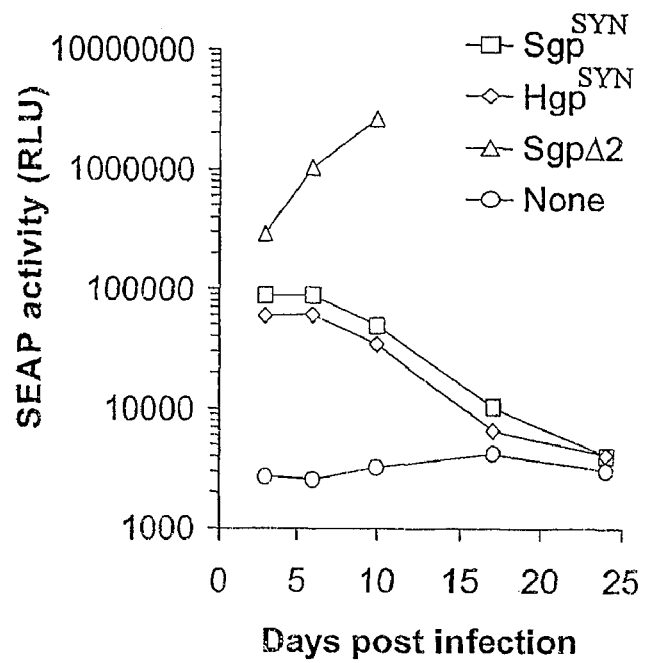

Detection of replication-competent recombinants. The potential emergence of replication competent recombinants (RCR) from our vector preparation was analysed in CEMx174 cells, which support replication of SIV and SIV hybrid viruses utilising a heterologous env gene (Reiprich et al., 1997, J.Virol. 71, 3328-3331). These cells were infected with 0.5 ml of ViGΔBH vector preparations (for titers see example 6, Table 2) packaged by SgpΔ2, Sgp$^{syn}$, or Hgp$^{syn}$ and pHIT-G. Slightly elevated capsid antigen levels (<400 pg SIVp27CA/ml) could be detected one and four days after infection. This has been observed previously and is probably due to carry over CA-antigen from the vector preparation (Schnell et al., 2000, Hum.Gene Ther. 11, 439-447). More importantly, CA antigen levels were below the level of detection of 20 pg SIVp27/ml two to eight weeks after infection in all cultures and no cytopathic effects could be observed. Therefore, the titer of a potential RCR is below 2 infectious unit/ml. Since no RCR could be detected with the wild-type SIV-gag-pol expression plasmid, SgpΔ2, this assay did not reveal potential advantages of the synthetic gag-pol expression plasmids. We therefore tested the frequency of emergence of RCR in an assay system, that would only require two homologous recombination events. SgpΔ2, Sgp$^{syn}$, or Hgp$^{syn}$ was cotransfected with either of two SIV vectors, that still contained env, vif, vpr, vpx, tat, and rev in addition to the GFP reporter gene, but which contained large deletions in gag-pol. The CEMx174-SIV-SEAP cells, which release SEAP after infection with SIV due to Tat transactivation (Means et al., 1997, J.Virol. 71, 7895-7902), were infected with 1 ml of the supernatant of the transfected cells. Three days after infection elevated SEAP activity was observed in cultures infected with the SIV vectors packaged by the synthetic gag-pol expression plasmids (FIG. 8). This should be due to transcomplementation of gag-pol and subsequent transfer of the SIV vector. However, the SEAP activity returned to background levels during the next 3 weeks (FIG. 8) indicating the absence of RCR. In contrast, increasing SEAP activity three to ten days after infection revealed rapid emergence of RCR in SIV vectors packaged by SgpΔ2. This was accompanied by extensive syncytia formation and cell death. Using a limiting dilution approach, the titer of the RCR in the supernatant of cells transfected with SgpΔ2 and SIV-GFPΔDP or SgpΔ2 and SIV-GFPΔBP was determined to be 130 and 75 TCID$_{50}$/ml, respectively. This demonstrates that if RCR emerge at all with the synthetic gag-pol genes, the frequency is at least reduced by a factor of approximately 100 in comparison to a wild-type gag-pol expression plasmid.

The invention claimed is:

1. A retroviral gag- or gagpol-based vector particle comprising a retroviral vector construct, wherein the packaging proteins are derived from retroviruses and are encoded by:
    an isolated nucleic acid molecule comprising a sequence encoding retroviral Gag and GagPol polypeptides, wherein from nucleotide 1 to nucleotide 489 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequence having the wild-type sequence.

2. The retroviral vector particle according to claim 1, wherein from nucleotide 1 to nucleotide 150 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Tip is encoded only by tgg, Tyr is encoded only by tac or tat, Val is encoded only by gtg or gtc and wherein the remaining 3'-sequence having the wild-type sequence.

3. The retroviral vector particle according to claim 1, wherein the retrovirus is selected from the group consisting of oncoviruses, spumaviruses and lentiviruses.

4. The retroviral vector particle according to claim 1, wherein the retrovirus is selected from the group consisting of HTLV-1, HTLV-2, HIV-1, HIV-2 and SIV.

5. The retroviral vector particle according to claim 4, wherein the retrovirus is HIV-1$_{IIIB}$ or SIV$_{mac239}$.

6. A retroviral gag- or gagpol-based vector particle comprising a retroviral vector construct, wherein the packaging proteins are derived from a first retrovirus and the vector construct is derived from a second retrovirus, and wherein the packaging proteins are derived from retroviruses and are encoded by:
    an isolated nucleic acid molecule comprising a sequence encoding retroviral Gag and GagPol polypeptides, wherein from nucleotide 1 to nucleotide 489 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequence having the wild-type sequence.

7. The retroviral vector particle according to claim 6, wherein from nucleotide 1 to nucleotide 150 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequence having the wild-type sequence.

8. The retroviral particle according to claim 6, wherein the first and second retrovirus are selected from the group consisting of oncoviruses, spumaviruses and lentiviruses.

9. The retroviral particle according to claim 6, wherein the first and second retrovirus are selected from the group consisting of HTLV-1, HTLV-2, HIV-1, HIV-2 and SIV.

10. The retroviral particle according to claim 9, wherein the first and second retrovirus are HIV-1$_{IIIB}$ and SIV$_{mac239}$, respectively.

11. A population of retroviral gag- or gagpol-based vector particles comprising retroviral vector constructs wherein, the packaging proteins are derived from retroviruses and are encoded by:
    an isolated nucleic acid molecule comprising a sequence encoding retroviral Gag and GagPol polypeptides, wherein from nucleotide 1 to nucleotide 489 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequences having the wild-type sequence.

12. A population of retroviral gag- or gagpol-based vector particles comprising retroviral vector constructs wherein, the packaging proteins are derived from retroviruses and are encoded by a nucleic acid selected from the group consisting of:
    an isolated nucleic acid molecule comprising a sequence encoding retroviral Gag and GagPol polypeptides, whereby from nucleotide 1 to nucleotide 489 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequences having the wild-type sequence, and wherein the population exhibits at least a at least a 100-fold reduction in recombination rate between said nucleic acid molecules encoding the gag and pol polypeptides and a wild-type vector construct derived from the same or another retrovirus.

13. A composition comprising a retroviral gag- or gagpol-based vector particle comprising a retroviral vector construct, wherein the packaging proteins are derived from retroviruses and are encoded by:

an isolated nucleic acid molecule comprising a sequence encoding retroviral Gag and GagPol polypeptides, wherein from nucleotide 1 to nucleotide 489 the amino acid Ala is encoded only by the nucleic acid triplet gcc or gct, Arg is encoded only by agg or aga, Asn is encoded only by aac or aat, Asp is encoded only by gac or gat, Cys is encoded only by tgc or tgt, Gln is encoded only by cag or caa, Glu is encoded only by gag or gaa, Gly is encoded only by ggc or gga, His is encoded only by cac or cat, Ile is encoded only by atc or att, Leu is encoded only by ctg or ctc, Lys is encoded only by aag or aaa, Met is encoded only by atg, Phe is encoded only by ttc or ttt, Pro is encoded only by ccc or cct, Ser is encoded only by agc or tcc, Thr is encoded only by acc or aca, Trp is encoded only by tgg, Tyr is encoded only by tac or tat, Val is encoded only by gtg or gtc and wherein the remaining 3'-sequences having the wild-type seequence; and a pharmaceutically-acceptable carrier or diluent.

14. The retroviral particle according to claim 1, wherein the codon optimized 5'-sequence is from nucleotide 1 to 150, from 1 to 294, or from 1 to 489.

15. The retroviral particle according to claim 6, wherein the codon optimized 5'-sequence is from nucleotide 1 to 150, from 1 to 294, or from 1 to 489.

16. The population of retroviral particles according to claim 11, wherein the codon optimized 5'-sequence is from nucleotide 1 to 150, from 1 to 294, or from 1 to 489.

17. The population of retroviral particles according to claim 12, wherein the codon optimized 5'-sequence is from nucleotide 1 to 150, from 1 to 294, or from 1 to 489.

18. The composition according to claim 13, wherein the codon optimized 5'-sequence is from nucleotide 1 to 150, from 1 to 294, or from 1 to 489.

* * * * *

SEQUENCE LISTING

<160> NUMBER OF SEQ ID NOS: 10

<210> SEQ ID NO 1
<211> LENGTH: 4358
<212> TYPE: DNA
<213> ORGANISM: Artificial Sequence
<220> FEATURE:
<223> OTHER INFORMATION: Synthetic

<400> SEQUENCE: 1

```
atgggcgtga ggaacagcgt gctgagcggc aagaaggccg acgagctgga gaagatcagg      60
ctgaggccca acggcaagaa gaagtatatg ctgaagcacg tggtgtgggc cgccaacgag     120
ctggacaggt tcggcctggc cgagagcctg ctggagaaca aggagggctg ccagaagatc     180
ctgagcgtgc tggccccccct ggtgcccacc ggcagcgaga acctgaagag cctgtacaac     240
accgtgtgcg tgatctggtg catccacgcc gaggagaagg tgaagcacac cgaggaggcc     300
aagcagatcg tgcagaggca cctggtggtg gagaccggcc ccaccgagac catgcccaag     360
accagcaggc ccaccgcccc cagctccggc cgcggcggca actacccgt gcagcagatc     420 ggcggcaact acgtgcacct gccccctgagc cccaggaccc tgaacgcctg ggtgaagctg     480
atcgaggaga agaagttcgg cgccgaggtg gtgcccggct ccaggcccct gagcgagggc     540 tgcaccccctt acgacatcaa ccagatgctg aactgcgtgg gcgaccacca ggccgccatg     600
cagatcatca gggacatcat caacgaggag gccgccgact gggacctgca gcaccctcag     660 cccgccccctc agcagggcca gctgagggag cccagcggca gcgacatcgc cggcaccaca     720
agcagcgtgg acgagcagat ccagtggatg tacaggcagc agaaccctat ccccgtgggc     780
aacatctaca ggaggtggat ccagctgggc ctccagaagt gcgtgaggat gtacaacccc     840
acaaacatcc tggacgtgaa gcagggacca aaggagccct tccagtcata tgtggacagg     900
ttctacaaga gcctgagggc cgagcagacc gacgccgccg tgaagaactg gatgacccag     960
accctgctga tccagaacgc caaccccgac tgcaagctgg tgctgaaggg cctgggcgtg    1020
aaccccaccc tggaggagat gctgaccgcc tgccagggc tgggcggccc cggccagaag    1080
gctaggctga tggccgaggc tctgaaggag gcctggccc ccgtgcccat cccccttcgcc    1140 gccgcccagc agagggggacc caggaagccc atcaagtgct ggaactgcgg caaggagggc    1200
cacagcgcca ggcagtgcag ggccccccagg aggcagggct gctggaagtg cggcaagatg    1260
gaccacgtga tggccaagtg ccccgacagg caggccggtt ttttaggcct tggtccatgg    1320
ggaaagaagc cccgcaattt cccccatggct caagtgcatc aggggctgat gccaactgct    1380
cccccagagg acccagctgt ggatctgcta aagaactaca tgcagttggg caagcagcag    1440
agagaaaagc agagagaaag cagagagaag ccttacaagg aggtgacaga ggatttgctg    1500
cacctcaatt ctctctttgg aggagaccag tagtgaccgc ccacatcgag ggccagcccg    1560
tggaggtgct gctggacacc ggcgccgacg acagcatcgt gaccggcatc gagctgggac    1620
cccactacac ccccaagatc gtgggcggca tcggcggctt catcaacaca aaggagtaca    1680
agaacgtgga gatcgaggtg ctgggcaaga ggatcaaggg caccatcatg accggcgaca    1740
cccccatcaa catcttcggc aggaacctgc tgaccgcccct gggcatgagc ctgaacttcc    1800
ccatcgccaa ggtggagccc gtgaaggtgg ccctgaagcc cggcaaggac ggccccaagc    1860
```

```
tgaagcagtg gcctctgagc aaggagaaga tcgtggccct gagggaaatc tgcgagaaga    1920
tggagaagga cggccagctg gaggaggccc ctcccaccaa cccctacaac acccccacct    1980
tcgccatcaa gaagaaggac aagaacaagt ggaggatgct gatcgacttc agggagctga    2040
acagggtgac acaggacttc accgaggtgc agctgggcat ccctcacccc gccggcctgg    2100
ccaagaggaa gaggatcacc gtgctggaca tcggcgacgc ctacttcagc atccctctgg    2160
acgaggagtt caggcagtac accgccttca ccctgcccag cgtgaacaac gccgagcccg    2220
gcaagaggta catctacaag gtgctgcccc agggctggaa gggcagcccc gccatcttcc    2280
agtacaccat gaggcacgtg ctggagccct tcaggaaggc caaccccgac gtgaccctgg    2340
tgcagtacat ggacgacatc ctgatcgcct ccgacaggac cgacctggag cacgacaggg    2400
tggtgctcca gagcaaggag ctgctgaaca gcatcggctt cagcaccccc gaggagaagt    2460
tccagaagga ccctccctcc cagtggatgg gctacgagct gtggcccacc aagtggaagc    2520
tccagaagat cgagctgccc cagagggaga cctggaccgt gaacgacatc cagaagctgg    2580
tgggcgtgct gaactgggcc gcccagattt accccggcat caagaccaag cacctgtgca    2640
ggctgatccg cggcaagatg acactgaccg aggaggtgca gtggaccgag atggccgagg    2700
ccgagtacga ggagaacaag atcattctga gccaggagca ggagggctgc tactaccagg    2760
agggcaagcc cctggaggcc accgtgatca agagccagga caaccagtgg agctacaaga    2820
tccaccagga ggacaagatc ctgaaggtgg gcaagttcgc caagatcaag aacacccaca    2880
ccaacggcgt gaggctgctg gcccacgtga tccagaagat cggcaaggag ccatcgtga    2940 tctggggcca ggtgcccaag ttccacctgc ccgtggagaa ggacgtgtgg gagcagtggt    3000
ggaccgacta ctggcaggtg acatggatcc ccgagtggga cttcatcagc accccctcctc    3060 tggtgaggct ggtgttcaat ctggtgaagg accccatcga gggcgaggag acctactaca    3120
ccgacggcag ctgcaacaag cagagcaagg agggcaaggc cggctacatc accgacaggg    3180
gcaaggacaa ggtgaaggtg ctggagcaga ccaccaacca gcaggccgag ctggaggcct    3240
tcctgatggc cctgaccgac agcggcccca aggccaacat catcgtggac agccagtatg    3300
tgatgggcat catcaccggc tgccccaccg agagcgagag caggctggtg aaccagatca    3360
tcgaggagat gattaagaag agcgagattt acgtggcctg ggtgcccgcc cacaagggca    3420
tcggcggcaa ccaggagatc gaccacctgg tgagccaggc catcaggcag gtgctgttcc    3480
tggagaagat cgagcccgcc caggaggagc acgacaagta ccacagcaac gtgaaggagc    3540
tggtgttcaa gttcggcctg cccaggatcg tggccaggca gatcgtggac acctgcgaca    3600
agtgccacca gaagggcgag gccatccacg gccaggccaa cagcgacctg ggcacctggc    3660
agatggactg cacccacctg gagggcaaga tcatcatcgt ggccgtgcac gtggctagcg    3720
gcttcatcga ggccgaggtg atccctcagg agaccggcag gcagaccgcc ctgttcctgc    3780
tgaagctggc cggcaggtgg cccatcaccc acctgcacac cgacaacggc gccaacttcg    3840
ccagccagga ggtgaagatg gtggcctggt gggccggcat cgagcacacc ttcggcgtgc    3900
cctacaaccc ccagagccag ggcgtggtgg aggccatgaa ccaccacctg aagaaccaga    3960
tcgacaggat cagggagcag gccaacagct ggagaccat cgtgctgatg gccgtgcact    4020
gcatgaactt caagaggagg ggcggcatcg gcgacatgac ccccgccgag aggctgatca    4080
acatgattac caccgagcag gagatccagt tccagcagag caagaacagc aagttcaaga    4140
acttcagggt gtattacagg gagggcaggg accagctgtg gaagggcccc ggcgagctgc    4200
tgtggaaggg cgagggcgct gtgatcctga aggtgggcac cgacatcaag gtggtgccca    4260
```

```
ggaggaaggc caagatcatc aaggactacg gcggcggcaa ggaggtggac agcagcagcc    4320
acatggagga caccggcgag gccagggagg tggcctga                           4358

<210> SEQ ID NO 2
<211> LENGTH: 4343
<212> TYPE: DNA
<213> ORGANISM: Artificial Sequence
<220> FEATURE:
<223> OTHER INFORMATION: Synthetic

<400> SEQUENCE: 2
atgggcgcca gggccagcgt gctgagcggc ggcgagctgg acaggtggga gaagatcagg      60
ctgaggcccg gcggcaagaa gaagtataag ctgaagcaca tcgtgtgggc cagcagggag     120
ctggagaggt tcgccgtgaa ccccggcctg ctggagacca gcgagggctg caggcagatc     180
ctgggccagc tgcagcccag cctgcagacc ggcagcgagg agctgaggag cctgtacaac     240
accgtggcca ccctgtactg cgtgcaccag aggatcgaga tcaaggacac caaggaggcc     300
ctggacaaga tcgaggagga gcagaacaag tccaagaaga aggcccagca ggccgccgcc     360
gacaccggcc acagcagcca ggtgagccag aactacccca tcgtgcagaa catccagggc     420
cagatggtgc accaggccat cagccccagg accctgaacg cctgggtgaa ggtggtggag     480
gagaaggcct tcagccccga ggtgatcccc atgttcagcg ccctgagcga gggagccacc     540
ccccaggacc tgaacaccat gctgaacacc gtgggcggcc accaggccgc catgcagatg     600
ctgaaggaga ccatcaacga ggaggccgcc gagtgggaca gggtgcaccc cgtgcacgcc     660
ggccccatcg cccccggcca gatgagggag cccgcggca gcgacatcgc cggcaccacc     720 agcacccctgc aggagcagat cggctggatg accaacaacc cccccatccc cgtgggcgaa     780
atctacaaga ggtggatcat cctgggcctg aacaagatcg tgaggatgta cagccccacc     840
agcatcctgg atatcaggca gggccccaaa gagcccttca gggactacgt ggacaggttc     900
tacaagaccc tgcgcgccga gcaggccagc caggaggtga gaactggat gaccgagacc     960 ctgctggtgc agaacgccaa ccccgactgc aagaccatcc tgaaggccct gggacccgcc    1020
gccaccctgg aggagatgat gaccgcctgc caggcgtgg gcggcccgg ccacaaggcc    1080 agggtgctgg ccgaggccat gagccaggtg accaacaccg ccaccatcat gatgcagagg    1140
ggcaacttca ggaaccagag gaagatggtg aagtgcttca ctgcggcaa ggagggccac    1200 accgccagga actgccgcgc ccccaggaag aagggctgct ggaagtgcgg caaggagggc    1260
caccagatga aggactgcac cgagaggcag gctaattttt tagggaagat ctggccttcc    1320
tacaagggaa ggccagggaa ttttcttcag agcagaccag agccaacagc cccaccattt    1380
cttcagagca gaccagagcc aacagcccca ccagaagaga gcttcaggtc tggggtagag    1440
acaacaactc cccctcagaa gcaggagccg atagacaagg aactgtatcc tttaacttcc    1500
ctcagatcac tctttggcaa cgaccccttcg tcacaataaa gatcggtggc agctgaagg    1560 aggccctgct ggacaccggc gccgacgaca ccgtgctgga ggagatgagc ctgcccggca    1620
ggtggaagcc caagatgatc ggcggcatcg gcggcttcat caaggtgagg cagtacgacc    1680
agatcctgat cgagatctgc ggccacaagg ccatcggcac cgtgctggtg ggccccaccc    1740
ccgtgaacat catcggcagg aacctgctga cccagatcg ctgcacctg aacttcccca    1800 tcagccccat cgagaccgtg cccgtgaagc tgaagcccgg catggacggc cctaaggtga    1860
agcagtggcc cctgaccgag gagaagatca aggcctggt ggagatctgc accgagatgg    1920
agaaggaggg caagatcagc aagatcggcc ccgagaaccc ctacaacacc cccgtgttcg    1980
```

```
ccatcaagaa gaaggacagc accaagtgga ggaagctggt ggacttcagg gagctgaaca    2040
agaggaccca ggacttctgg gaggtgcagc tgggcatccc ccaccccgcc ggcctgaaga    2100
agaagaagag cgtgaccgtg ctggacgtgg gcgacgccta cttcagcgtg ccctggacg     2160 aggacttcag gaagtatacc gccttcacca tccccagcat caacaacgag accccggca    2220 tccgctacca gtacaacgtg ctgccccagg gctggaaggg cagccccgcc atcttccaga    2280
gcagcatgac aaagatcctg gagcccttca gaagcagaa ccccgacatc gtgatctatc    2340
agtacatgga cgacctgtac gtgggcagcg acctggagat cggccagcac aggaccaaga    2400
tcgaggagct gaggcagcac ctgctgaggt ggggcctgac caccccgac aagaagcacc     2460 agaaggagcc cccattcctg tggatgggct acgagctgca ccccgacaag tggaccgtgc    2520
agcccatcgt gctgcccgag aaggacagct ggaccgtgaa cgacattcag aagctggtgg    2580
gcaagctgaa ctgggccagc cagatctacc ccggcatcaa ggtgaggcag ctgtgcaagc    2640
tgctgagggg cacaaaggct ctgaccgagg tgatccccct gaccgaggag ccgagctgg     2700 agctggccga gaacagggag atcctgaagg agcccgtgca cggcgtgtac tacgacccca    2760
gcaaggacct gatcgccgag atccagaagc agggccaggg ccagtggacc taccagatct    2820
accaggagcc cttcaagaac ctgaagaccg gcaagtacgc ccgcatgcgc ggcgcccaca    2880
ccaacgacgt gaagcagctg accgaggccg tgcagaagat caccaccgag agcatcgtga    2940 tctgggcaa gacccccaag ttcaagctgc ccatccagaa ggagacctgg gagacctggt     3000
ggaccgagta ctggcaggcc acctggattc ccgagtggga gttcgtgaac acccctcccc    3060
tggtgaagct gtggtatcag ctggagaagg agcccatcgt gggcgccgag accttctacg    3120
tggacggcgc cgccaacagg gagaccaagc tgggcaaggc cggctacgtg accaacaagg    3180
gccgccagaa ggtggtgccc ctgaccaaca ccaccaacca gaagaccgag ctgcaggcta    3240
tctacctggc cctgcaggac tcaggcctgg aggtgaacat cgtgaccgac agccagtacg    3300
ccctgggcat catccaggcc cagcccgaca agagcgagag cgagctggtg aaccagatca    3360
tcgagcagct gatcaagaag gagaaggtgt acctggcctg ggtgccccc cacaagggca     3420 tcggcggcaa cgagcaggtg acaagctggt gagcgccgg catcaggaag atcctgttcc    3480
tggacggcat cgacaaggcc caggacgagc acgagaagta ccacagcaac tggagggcta    3540
tggctagcga cttcaacctg cctcccgtgg tggctaagga gatcgtggcc agctgcgaca    3600
agtgccagct gaagggcgag gccatgcacg gccaggtgga ctgcagcccc ggcatctggc    3660
agctggactg cacccacctg gagggcaagg tgatcctggt ggccgtgcac gtggcctccg    3720
gctacatcga ggccgaggtg atccccgccg agaccggcca ggagaccgcc tacttcctgc    3780
tgaagctggc cggccgctgg cccgtgaaga ccatccacac cgacaacggc agcaacttca    3840
ccagcgccac cgtgaaggcc gcctgctggt gggccggcat caagcaggag ttcggcatcc    3900
cctacaaccc ccagtctcag ggcgtggtgg agagcatgaa caaggagctg aagaagatca    3960
tcggccaggt gagggaccag gccgagcacc tgaagaccgc cgtgcagatg gccgtgttca    4020
tccacaactt caagaggaag gcggcatcg gcggctacag cgccggcgag aggatcgtgg    4080
acatcatcgc caccgacatc cagaccaagg agctgcagaa gcagatcacc aagatccaga    4140
acttcagggg tgtactacagg gacagcagga accctctgtg gaagggcccc gccaagctgc    4200
tgtggaaggg cgagggcgcc gtggtgatcc aggacaacag cgacatcaag gtggtgccca    4260
ggaggaaggc caagatcatc agggactacg gcaagcagat ggccggcgac gactgcgtgg    4320
cctccaggca ggacgaggac tga                                           4343
```

<210> SEQ ID NO 3
<211> LENGTH: 4341
<212> TYPE: DNA
<213> ORGANISM: Artificial Sequence
<220> FEATURE:
<223> OTHER INFORMATION: Synthetic

<400> SEQUENCE: 3

| | |
|---|---|
| atgggcgcca gggccagcgt gctgagcggc ggcgagctgg acaggtggga gaagatcagg | 60 |
| ctgaggcccg gcggcaagaa gaagtataag ctgaagcaca tcgtgtgggc cagcagggag | 120 |
| ctggagaggt tcgccgtgaa ccccggcctg ctggagacca gcgagggctg caggcagatc | 180 |
| ctgggccagc tgcagcccag cctgcagacc ggcagcgagg agctgaggag cctgtacaac | 240 |
| accgtggcca ccctgtactg cgtgcaccag aggatcgaga tcaaggacac caaggaggcc | 300 |
| ctggacaaga tcgaggagga gcagaacaag tccaagaaga aggcccagca ggccgccgcc | 360 |
| gacaccggcc acagcagcca ggtgagccag aactacccca tcgtgcagaa catccagggc | 420 |
| cagatggtgc accaggccat cagccccagg accctgaacg cctgggtgaa ggtggtggag | 480 |
| gagaaggcct tcagccccga ggtgatcccc atgttcagcg ccctgagcga gggagccacc | 540 |
| ccccaggacc tgaacaccat gctgaacacc gtgggcggcc accaggccgc catgcagatg | 600 |
| ctgaaggaga ccatcaacga ggaggccgcc gagtgggaca gggtgcaccc cgtgcacgcc | 660 |
| ggccccatcg cccccggcca gatgagggag cccgcggca gcgacatcgc cggcaccacc | 720 |
| agcacccctgc aggagcagat cggctggatg accaacaacc ccccatccc cgtgggcgaa | 780 |
| atctacaaga ggtggatcat cctgggcctg aacaagatcg tgaggatgta cagccccacc | 840 |
| agcatcctgg atatcaggca ggggccccaaa gagcccttca gggactacgt ggacaggttc | 900 |
| tacaagaccc tgcgcgccga gcaggccagc caggaggtga gaactggat gaccgagacc | 960 |
| ctgctggtgc agaacgccaa ccccgactgc aagaccatcc tgaaggccct gggacccgcc | 1020 |
| gccaccctgg aggagatgat gaccgcctgc caggccgtgg gcggcccccgg ccacaaggcc | 1080 |
| agggtgctgg ccgaggccat gagccaggtg accaacaccg ccaccatcat gatgcagagg | 1140 |
| ggcaacttca ggaaccagag gaagatggtg aagtgcttca actgcggcaa ggagggccac | 1200 |
| accgccagga actgccgcgc ccccaggaag aagggctgct ggaagtgcgg caaggagggc | 1260 |
| caccagatga aggactgcac cgagaggcag gctaatttta gggaagatct ggccttccta | 1320 |
| caagggaagg ccagggaatt ttcttcagag cagaccagag ccaacagccc caccatttct | 1380 |
| tcagagcaga ccagagccaa cagccccacc agaagagagc ttcaggtctg ggtagagac | 1440 |
| aacaactccc cctcagaagc aggagccgat agacaaggaa ctgtatcctt taacttccct | 1500 |
| cagatcactc tttggcaacg acccctcgtc acaataaaga tcggtggcca gctgaaggag | 1560 |
| gccctgctgg acaccggcgc cgacgacacc gtgctggagg agatgagcct gccccggcagg | 1620 |
| tggaagccca agatgatcgg cggcatcggc ggcttcatca aggtgaggca gtacgaccag | 1680 |
| atcctgatcg agatctgcgg ccacaaggcc atcggcaccg tgctggtggg ccccaccccc | 1740 |
| gtgaacatca tcggcaggaa cctgctgacc cagatcggct gcaccctgaa cttccccatc | 1800 |
| agccccatcg agaccgtgcc cgtgaagctg aagcccggca tggacggccc taaggtgaag | 1860 |
| cagtggcccc tgaccgagga aagatcaag gccctggtgg agatctgcac cgagatggag | 1920 |
| aaggagggca agatcagcaa gatcggcccc gagaacccct acaacacccc cgtgttcgcc | 1980 |
| atcaagaaga aggacagcac caagtggagg aagctggtgg acttcaggga gctgaacaag | 2040 |
| aggacccagg acttctggga ggtgcagctg ggcatccccc accccgccgg cctgaagaag | 2100 |

```
aagaagagcg tgaccgtgct ggacgtgggc gacgcctact tcagcgtgcc cctggacgag    2160
gacttcagga agtataccgc cttcaccatc cccagcatca acaacgagac ccccggcatc    2220
cgctaccagt acaacgtgct gccccagggc tggaagggca gccccgccat cttccagagc    2280
agcatgacaa agatcctgga gcccttcaag aagcagaacc ccgacatcgt gatctatcag    2340
tacatggacg acctgtacgt gggcagcgac ctggagatcg ccagcacag gaccaagatc    2400 gaggagctga ggcagcacct gctgaggtgg ggcctgacca cccccgacaa gaagcaccag    2460
aaggagcccc cattcctgtg gatgggctac gagctgcacc ccgacaagtg gaccgtgcag    2520
cccatcgtgc tgcccgagaa ggacagctgg accgtgaacg acattcagaa gctggtgggc    2580
aagctgaact gggccagcca gatctacccc ggcatcaagg tgaggcagct gtgcaagctg    2640 ctgagggca caaaggctct gaccgaggtg atccccctga ccgaggaggc cgagctggag    2700
ctggccgaga cagggagat cctgaaggag cccgtgcacg gcgtgtacta cgaccccagc    2760
aaggacctga tcgccgagat ccagaagcag ggccagggcc agtggaccta ccagatctac    2820
caggagccct tcaagaacct gaagaccggc aagtacgccc gcatgcgcgg cgcccacacc    2880
aacgacgtga agcagctgac cgaggccgtg cagaagatca ccaccgagag catcgtgatc    2940
tggggcaaga cccccaagtt caagctgccc atccagaagg agacctggga gacctggtgg    3000
accgagtact ggcaggccac ctggattccc gagtgggagt tcgtgaacac ccctcccctg    3060
gtgaagctgt ggtatcagct ggagaaggag cccatcgtgg gcgccgagac cttctacgtg    3120
gacggcgccg ccaacaggga gaccaagctg ggcaaggccg gctacgtgac caacaagggc    3180
cgccagaagg tggtgcccct gaccaacacc accaaccaga gaccgagct gcaggctatc    3240 tacctggccc tgcaggactc aggcctggag gtgaacatcg tgaccgacag ccagtacgcc    3300
ctgggcatca tccaggccca gcccgacaag agcgagagcg agctggtgaa ccagatcatc    3360
gagcagctga tcaagaagga gaaggtgtac ctggcctggg tgcccgccca aagggcatc    3420 ggcggcaacg agcaggtgga caagctggtg agcgccggca tcaggaagat cctgttcctg    3480
gacggcatcg acaaggccca ggacgagcac gagaagtacc acagcaactg gagggctatg    3540
gctagcgact tcaacctgcc tcccgtggtg gctaaggaga tcgtggccag ctgcgacaag    3600
tgccagctga gggcgaggc catgcacggc caggtggact gcagccccgg catctggcag    3660
ctggactgca cccacctgga gggcaaggtg atcctggtgg ccgtgcacgt ggcctccggc    3720
tacatcgagg ccgaggtgat ccccgccgag accggccagg agaccgccta cttcctgctg    3780
aagctggccg gccgctggcc cgtgaagacc atccacaccg acaacggcag caacttcacc    3840
agcgccaccg tgaaggccgc ctgctggtgg gccggcatca gcaggagtt cggcatcccc    3900 tacaaccccc agtctcaggg cgtggtggag agcatgaaca aggagctgaa gaagatcatc    3960
ggccaggtga ggaccaggc cgagcacctg aagaccgccg tgcagatggc cgtgttcatc    4020
cacaacttca gaggaaggg cggcatcggc ggctacagcg ccggcgagag gatcgtggac    4080
atcatcgcca ccgacatcca gaccaaggag ctgcagaagc agatcaccaa gatccagaac    4140
ttcagggtgt actacaggga cagcaggaac cctctgtgga agggccccgc caagctgctg    4200
tggaagggcg agggcgccgt ggtgatccag gacaacagcg acatcaaggt ggtgcccagg    4260
aggaaggcca agatcatcag ggactacggc aagcagatgg ccggcgacga ctgcgtggcc    4320
tccaggcagg acgaggactg a                                              4341

<210> SEQ ID NO 4
<211> LENGTH: 3981
```

```
<212> TYPE: DNA
<213> ORGANISM: Artificial Sequence
<220> FEATURE:
<223> OTHER INFORMATION: Synthetic

<400> SEQUENCE: 4
atggccgcca gggccagcgt gctgagcggc ggcgagctgg acaggtggga gaagatcagg    60
ctgaggcccg gcggcaagaa gaagtataag ctgaagcaca tcgtgtgggc cagcagggag   120
ctggagaggt tcgccgtgaa ccccggcctg ctggagacca gcgagggctg caggcagatc   180
ctgggccagc tgcagcccag cctgcagacc ggcagcgagg agctgaggag cctgtacaac   240
accgtggcca ccctgtactg cgtgcaccag aggatcgaga tcaaggacac caaggaggcc   300
ctggacaaga tcgaggagga gcagaacaag tccaagaaga aggcccagca ggccgccgcc   360
gacaccggcc acagcagcca ggtgagccag aactacccca tcgtgcagaa catccagggc   420
cagatggtgc accaggccat cagccccagg accctgaacg cctgggtgaa ggtggtggag   480
gagaaggcct tcagccccga ggtgatcccc atgttcagcg ccctgagcga gggagccacc   540
cccaggacc tgaacaccat gctgaacacc gtgggcggcc accaggccgc catgcagatg   600
ctgaaggaga ccatcaacga ggaggccgcc gagtgggaca gggtgcaccc cgtgcacgcc   660
ggccccatcg cccccggcca gatgagggag cccgcggca gcgacatcgc cggcaccacc   720
agcaccctgc aggagcagat cggctggatg accaacaacc cccccatccc cgtgggcgaa   780
atctacaaga ggtggatcat cctgggcctg aacaagatcg tgaggatgta cagccccacc   840
agcatcctgg atatcaggca gggccccaaa gagcccttca gggactacgt ggacaggttc   900
tacaagaccc tgcgcgccga gcaggccagc caggaggtga gaactggat gaccgagacc   960
ctgctggtgc agaacgccaa ccccgactgc aagaccatcc tgaaggccct gggacccgcc  1020
gccaccctgg aggagatgat gaccgcctgc cagggcgtgg gcggccccgg ccacaaggcc  1080
agggtgctgg ccgaggccat gagccaggtg accaacaccg ccaccatcat gatgcagagg  1140
ggcaacttca ggaaccagag gaagatggtg aagtgcttca ctgcggcaa ggagggccac  1200
accgccagga actgccgcgc ccccaggaag aagggctgct ggaagtgcgg caaggagggc  1260
caccagatga aggactgcac cgagaggcag gctaatttta gggaagatct ggccttccta  1320
caagggaagg ccagggaatt ttcttcagag cagaccagag ccaacagccc caccatttct  1380
tcagagcaga ccagagccaa cagccccacc agaagagagc ttcaggtctg ggtagagac  1440
aacaactccc cctcagaagc aggagccgat agacaaggaa ctgtatcctt aacttccct  1500
cagatcactc tttggcaacg accctcgtc acaataaaga tcggtggcca gctgaaggag  1560
gccctgctgg ccaccggcgc cgacgacacc gtgctggagg agatgagcct gcccggcagg  1620
tggaagccca agatgatcgg cggcatcggc ggcttcatca aggtgaggca gtacgaccag  1680
atcctgatcg agatctgcgg ccacaaggcc atcggcaccg tgctggtggg acctacacct  1740
gtgaacatca tcgcaggaa cctgctgacc cagatcggct gcaccctgaa cttccccatc  1800
agccccatcg agaccgtgcc cgtgaagctg aagcccggca tggacggccc taaggtgaag  1860
cagtggcccc tgaccgagga gaagatcaag gccctggtgg agatctgcac cgagatggag  1920
aaggagggca gatcagcaa gatcggcccc gagaacccct acaacacccc cgtgttcgcc  1980
atcaagaaga aggacagcac caagtggagg aagctggtgg acttcaggga gctgaacaag  2040
aggacccagg acttctggga ggtgcagctg ggcatccccc accccgccgg cctgaagaag  2100
aagaagagcg tgaccgtgct ggacgtgggc gacgcctact cagcgtgcc cctggacgag  2160
gacttcagga gtatacccc tttaagacca atgacttaca aggcagctgt agatcttagc  2220
```

| | |
|---|---|
| cacttttta aagaaaaggg gggactggaa gggctaattc actcccaaag aagacaagat | 2280 |
| atccttgatc tgtggatcta ccacacacaa ggctacttcc ctgatccaag gatgggtggc | 2340 |
| aagtggtcaa aaagtagtgt ggttggatgg cctgctgtaa gggaaagaat gagacgagct | 2400 |
| gagccagcag cagatggggt gggagcagca tctcgagacc tggaaaaaca tggagcaatc | 2460 |
| acaagtagca atacagcagc taccaatgct gcttgtgcct ggctagaagc acaagaggag | 2520 |
| gaggaggtgg gttttccagt cacacctcaa gtaccattcc tgtggatggg ctacgagctg | 2580 |
| caccccgaca gtggaccgt gcagcccatc gtgctgcccg agaaggacag ctggaccgtg | 2640 |
| aacgacattc agaagctggt gggcaagctg aactgggcca gccagatcta ccctggcatc | 2700 |
| aaggtgaggc agctgtgcaa gctgctgagg ggcacaaagg ctctgaccga ggtgatcccc | 2760 |
| ctgaccgagg aggccgagct ggagctggcc gagaacaggg agatcctgaa ggagcccgtg | 2820 |
| cacggcgtgt actacgaccc cagcaaggac ctgatcgccg agatccagaa gcagggccag | 2880 |
| ggccagtgga cctaccagat ctaccaggag cccttcaaga acctgaagac cggcaagtac | 2940 |
| gcccgcatgc gcggcgccca caccaacgac gtgaagcagc tgaccgaggc cgtgcagaag | 3000 |
| atcaccaccg agagcatcgt gatctggggc aagactccta agttcaagct gcccatccag | 3060 |
| aaggagacct gggagacctg gtggaccgag tactggcagg ccacctggat tcccgagtgg | 3120 |
| gagttcgtga acacccctcc cctggtgaag ctgtggtatc agctggagaa ggagcccatc | 3180 |
| gtgggcgccg agaccttcta cgtggacggc gccgccaaca gggagaccaa gctgggcaag | 3240 |
| gccggctacg tgaccaacaa gggccgccag aaggtggtgc ccctgaccaa caccaccaac | 3300 |
| cagaagaccg agctgcaggc tatctacctg gccctgcagg actcaggcct ggaggtgaac | 3360 |
| atcgtgaccg acagccagta cgccctgggc atcatccagg cccagcccga caagagcgag | 3420 |
| agcgagctgg tgaaccagat catcgagcag ctgatcaaga aggagaaggt gtacctggcc | 3480 |
| tgggtgcccg cccacaaggg catcggcggc aacgagcagg tggacaagct ggtgagcgcc | 3540 |
| ggcatcagga agatcctgtt cctggacggc atcgacaagg cccaggacga gcacgagaag | 3600 |
| taccacagca actggagggc tatggctagc gacttcaacc tgcctcccgt ggtggctaag | 3660 |
| gagatcgtgg ccagcgcctt caccatcccc agcatcaaca acgagacccc cggcatccgc | 3720 |
| taccagtaca acgtgctgcc ccagggctgg aagggcagcc ccgccatctt ccagagcagc | 3780 |
| atgacaaaga tcctggagcc cttcaagaag cagaaccccg acatcgtgat ctatcagtac | 3840 |
| atggacgacc tgtacgtggg cagcgacctg gagatcggcc agcacaggac caagatcgag | 3900 |
| gagctgaggc agcacctgct gaggtggggc ctgaccaccc ccgacaagaa gcaccagaag | 3960 |
| gagcccccat tcctgtggta a | 3981 |

<210> SEQ ID NO 5
<211> LENGTH: 1539
<212> TYPE: DNA
<213> ORGANISM: Artificial Sequence
<220> FEATURE:
<223> OTHER INFORMATION: Synthetic

<400> SEQUENCE: 5

| | |
|---|---|
| atgggcgcca gggccagcgt gctgagcggg ggcgagctgg acaggtggga gaagatcagg | 60 |
| ctgaggcccg gcggcaagaa gaagtataag ctgaagcaca tcgtgtgggc cagcagggag | 120 |
| ctggagaggt tcgccgtgaa ccccggcctg ctggagacca gcgagggctg caggcagatc | 180 |
| ctgggccagc tgcagcccag cctgcagacc ggcagcgagg agctgaggag cctgtacaac | 240 |
| accgtggcca ccctgtactg cgtgcaccag aggatcgaga tcaaggacac caaggaggcc | 300 |

-continued

```
ctggacaaga tcgaggagga gcagaacaag tccaagaaga aggcccagca ggccgccgcc      360
gacaccggcc acagcagcca ggtgagccag aactacccca tcgtgcagaa catccagggc      420
cagatggtgc accaggccat cagccccagg accctgaacg cctgggtgaa ggtggtggag      480
gagaaggcct tcagccccga ggtgatcccc atgttcagcg ccctgagcga gggagccacc      540
ccccaggacc tgaacaccat gctgaacacc gtgggcggcc accaggccgc catgcagatg      600
ctgaaggaga ccatcaacga ggaggccgcc gagtgggaca gggtgcaccc cgtgcacgcc      660
ggccccatcg ccccggcca gatgaggag ccccgcggca gcgacatcgc cggcaccacc       720
agcaccctgc aggagcagat cggctggatg accaacaacc ccccatccc cgtgggcgaa      780 atctacaaga ggtggatcat cctgggcctg aacaagatcg tgaggatgta cagccccacc      840
agcatcctgg atatcaggca gggcccccaaa gagcccttca gggactacgt ggacaggttc     900
tacaagaccc tgcgcgccga gcaggccagc caggaggtga agaactggat gaccgagacc      960
ctgctggtgc agaacgccaa cccgactgc aagaccatcc tgaaggccct gggacccgcc      1020
gccaccctgg aggagatgat gaccgcctgc cagggcgtgg gcggccccgg ccacaaggcc      1080
agggtgctgg ccgaggccat gagccaggtg accaacaccg ccaccatcat gatgcagagg      1140
ggcaacttca ggaaccagag gaagatggtg aagtgcttca actgcggcaa ggagggccac      1200
accgccagga actgccgcgc ccccaggaag aagggctgct ggaagtgcgg caaggagggc      1260
caccagatga aggactgcac cgagaggcag gccaacttcc tgggcaagat ctggcccagc      1320
tacaagggca ggcccggcaa cttcctgcag agcaggcccg agcccaccgc cccccccttc      1380
ctgcagagca ggcccgagcc caccgccccc ccgaggaga gcttcaggag cggcgtggag       1440
accaccaccc ctcctcagaa gcaggagccc atcgacaagg agctgtaccc cctgaccagc      1500
ctgaggagcc tgttcggcaa cgaccccagc agccagtga                             1539

<210> SEQ ID NO 6
<211> LENGTH: 35
<212> TYPE: DNA
<213> ORGANISM: Artificial Sequence
<220> FEATURE:
<223> OTHER INFORMATION: Synthetic

<400> SEQUENCE: 6
gcgggtaccg aattccgacg caggactcgg cttgc                                 35

<210> SEQ ID NO 7
<211> LENGTH: 51
<212> TYPE: DNA
<213> ORGANISM: Artificial Sequence
<220> FEATURE:
<223> OTHER INFORMATION: Synthetic

<400> SEQUENCE: 7
gccgagctcc tcgagggatc cttattgtga cgaggggtcg ttgccaaaga g               51

<210> SEQ ID NO 8
<211> LENGTH: 51
<212> TYPE: DNA
<213> ORGANISM: Artificial Sequence
<220> FEATURE:
<223> OTHER INFORMATION: Synthetic

<400> SEQUENCE: 8
gcgggtaccg aattcaggag agagatgggt gcgagagcgt cagtattaag c               51
```

```
<210> SEQ ID NO 9
<211> LENGTH: 32
<212> TYPE: DNA
<213> ORGANISM: Artificial Sequence
<220> FEATURE:
<223> OTHER INFORMATION: Synthetic

<400> SEQUENCE: 9
ggatggcgcc catctctctc cttctagcct cc                                    32

<210> SEQ ID NO 10
<211> LENGTH: 1527
<212> TYPE: DNA
<213> ORGANISM: Artificial Sequence
<220> FEATURE:
<223> OTHER INFORMATION: Synthetic

<400> SEQUENCE: 10
atgggtgcga gagcgtcagt attaagcggg ggagaattag atcgatggga aaaaattcgg      60
ttaaggccag ggggaaagaa aaatatataa ttaaaacata tagtatgggc aagcagggag     120
ctagaacgat tcgcagttaa tcctggcctg ttagaaacat cagaaggctg tagacaaata     180
ctggcacagc tacaaccatc ccttcagaca ggatcagaag aacttagatc attatataat     240
acagtagcaa ccctctattg tgtgcatcaa aggatagaga taaaagacac caaggaagct     300
ttagacaaga tagaggaaga gcaaaacaaa agtaagaaaa agcacagca agcagcagct     360 gacacaggac acagcagtca ggtcagccaa aattacccta tagtgcagaa catccagggg     420
caaatggtac atcaggccat atcacctaga actttaaatg catgggtaaa agtagtagaa     480
gagaaggctt tcagcccaga agtaataccc atgttttcag cattatcaga aggagccacc     540
ccacaagatt taaacaccat gctaaacaca gtggggggac atcaagcagc catgcaaatg     600
ttaaaagaga ccatcaatga ggaagctcca gaatgggata gagtacatcc agtgcatgca     660
gggcctattg caccaggcca gatgagagaa ccaaggggaa gtgacatagc aggaactact     720
agtacccttc aggaacaaat aggatggatg acaaataatc cacctatccc agtaggagaa     780
atttataaaa gatggataat cctgggatta aataaaatag taagaatgta tagccctacc     840
agcattctgg acataagaca aggaccaaaa gaaccttttta gagactatgt agaccggttc     900
tataaaactc taagagccga gcaagcttca caggaggtaa aaaattggat gacagaaacc     960
ttgttggtcc aaaatgcgaa cccagattgt aagactattt taaaagcatt gggaccagcg    1020
gctacactag aagaaatgat gacagcatgt cagggagtag gaggacccgg ccataaggca    1080
agagttttgg ctgaagcaat gagccaagta acaaatacag ctaccataat gatgcagaga    1140
ggcaatttta ggaaccaaag aaagatggtt aagtgtttca attgtggcaa agaagggcac    1200
acagccagaa attgcagggc ccctaggaaa aagggctgtt ggaaatgtgc aaggaagga    1260 caccaaatga aagattgtac tgagagacag gctaattttt tagggaagat ctggccttcc    1320
tacaagggaa ggccagggaa ttttcttcag agcagaccag agccaacagc cccaccattt    1380
cttcagagca gaccagagcc aacagcccca ccagaagaga gcttcaggtc tggggtagag    1440
acaacaactc cccctcagaa gcaggagccg atagacaagg aactgtatcc tttaacttcc    1500
ctcagatcac tctttggcaa cgacccc                                      1527
```